(12) United States Patent
Erskine

(10) Patent No.: US 8,968,240 B2
(45) Date of Patent: *Mar. 3, 2015

(54) METHOD OF MAKING A NEEDLE SHIELDING DEVICE

(75) Inventor: Timothy J. Erskine, Sandy, UT (US)

(73) Assignee: Erskine Medical LLC, High Falls, NY (US)

( * ) Notice: Subject to any disclaimer, the term of this patent is extended or adjusted under 35 U.S.C. 154(b) by 1118 days.

This patent is subject to a terminal disclaimer.

(21) Appl. No.: 11/817,892

(22) PCT Filed: Mar. 6, 2006

(86) PCT No.: PCT/US2006/007909
§ 371 (c)(1),
(2), (4) Date: Sep. 6, 2007

(87) PCT Pub. No.: WO2006/096633
PCT Pub. Date: Sep. 14, 2006

(65) Prior Publication Data
US 2009/0249605 A1 Oct. 8, 2009

Related U.S. Application Data

(60) Provisional application No. 60/659,213, filed on Mar. 7, 2005, provisional application No. 60/659,217, filed on Mar. 7, 2005, provisional application No. 60/659,226, filed on Mar. 7, 2005, provisional application No. 60/714,954, filed on Sep. 7, 2005.

(51) Int. Cl.
 *A61M 25/06* (2006.01)
 *A61M 5/158* (2006.01)
 *A61M 5/32* (2006.01)

(52) U.S. Cl.
 CPC ........... *A61M 25/0631* (2013.01); *A61M 5/158* (2013.01); *A61M 5/3269* (2013.01);
 (Continued)

(58) Field of Classification Search
 USPC ........ 604/110, 158, 162, 163, 164.01, 164.08
 See application file for complete search history.

(56) References Cited

U.S. PATENT DOCUMENTS 2,798,487 A 7/1957 Ferguson
3,459,183 A 8/1969 Ring et al.
(Continued)

FOREIGN PATENT DOCUMENTS

CN 1145813 A 3/1997
CN 1547493 A 11/2004
(Continued)

OTHER PUBLICATIONS

Erskine, Canadian Application No. 2,599,943, Office Action dated Dec. 30, 2010, 2 pages.
(Continued)

*Primary Examiner* — Nathan R Price
(74) *Attorney, Agent, or Firm* — Hoffman Warnick LLC

(57) ABSTRACT

Methods of manufacturing a catheter introducer or needle assembly and needle shield are disclosed. A needle shield has a blocking object (preferably a ball) which moves from an non-shielding position to a shielding position. The catheter introducer is made by placing the blocking object into the shield and inserting the proximal end of the needle into the shield while the blocking object is in the shielding position. The catheter introducer is made using extruded polymeric tubes which may have coextruded reinforcing.

9 Claims, 46 Drawing Sheets

(52) U.S. Cl.
CPC ............ *A61M5/3271* (2013.01); *A61M 5/3273* (2013.01); *A61M 25/0618* (2013.01); *A61M 25/0625* (2013.01); *A61M 2005/3247* (2013.01); *A61M 2005/325* (2013.01)
USPC .................................. 604/110; 604/164.08

(56) References Cited

U.S. PATENT DOCUMENTS

| | | |
|---|---|---|
| 4,588,398 A | 5/1986 | Daugherty et al. |
| 4,596,563 A | 6/1986 | Pande |
| 4,755,170 A | 7/1988 | Golden |
| 4,762,516 A | 8/1988 | Luther et al. |
| 4,778,453 A | 10/1988 | Lopez |
| 4,790,828 A | 12/1988 | Dombrowski et al. |
| 4,832,696 A | 5/1989 | Luther et al. |
| 4,834,718 A | 5/1989 | McDonald |
| 4,846,809 A | 7/1989 | Sims |
| 4,863,436 A | 9/1989 | Glick |
| 4,887,998 A | 12/1989 | Martin et al. |
| 4,927,414 A | 5/1990 | Kulli |
| 4,929,241 A | 5/1990 | Kulli |
| 4,931,048 A | 6/1990 | Lopez |
| 4,944,725 A | 7/1990 | McDonald |
| 4,952,207 A | 8/1990 | Lemieux |
| 4,978,344 A | 12/1990 | Dombrowski et al. |
| 5,049,136 A | 9/1991 | Johnson |
| 5,059,180 A | 10/1991 | McLees |
| 5,116,326 A | 5/1992 | Schmidt |
| 5,120,320 A | 6/1992 | Fayngold |
| 5,160,325 A | 11/1992 | Nichols et al. |
| 5,215,528 A | 6/1993 | Purdy et al. |
| RE34,416 E | 10/1993 | Lemieux |
| 5,261,895 A | 11/1993 | Kablik |
| 5,300,045 A | 4/1994 | Plassche, Jr. |
| 5,304,151 A | 4/1994 | Kuracina |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,360,408 A | 11/1994 | Vaillancourt |
| 5,360,497 A | 11/1994 | Schneider et al. |
| 5,376,075 A | 12/1994 | Haughton et al. |
| 5,429,611 A | 7/1995 | Rait |
| 5,447,501 A | 9/1995 | Karlsson et al. |
| 5,458,658 A | 10/1995 | Sircom |
| 5,466,223 A | 11/1995 | Bressler et al. |
| 5,558,651 A | 9/1996 | Crawford et al. |
| 5,582,597 A | 12/1996 | Brimhall et al. |
| 5,584,809 A | 12/1996 | Gaba |
| 5,599,310 A | 2/1997 | Bogert |
| 5,601,536 A | 2/1997 | Crawford et al. |
| 5,611,781 A | 3/1997 | Sircom et al. |
| 5,662,610 A | 9/1997 | Sircom |
| 5,669,927 A | 9/1997 | Boebel et al. |
| 5,683,365 A | 11/1997 | Brown et al. |
| 5,690,619 A | 11/1997 | Erskine |
| 5,697,907 A | 12/1997 | Gaba |
| 5,700,250 A | 12/1997 | Erskine |
| 5,718,688 A | 2/1998 | Wozencroft |
| 5,755,699 A | 5/1998 | Blecher et al. |
| 5,795,339 A | 8/1998 | Erskine |
| 5,853,393 A | 12/1998 | Bogert |
| 5,879,337 A | 3/1999 | Kuracina et al. |
| 5,951,515 A * | 9/1999 | Osterlind ...................... 604/110 |
| 5,951,525 A | 9/1999 | Thorne et al. |
| 6,001,080 A | 12/1999 | Kuracina et al. |
| 6,004,294 A | 12/1999 | Brimhall et al. |
| 6,117,108 A | 9/2000 | Woehr et al. |
| 6,210,371 B1 | 4/2001 | Shaw |
| 6,221,047 B1 | 4/2001 | Greene et al. |
| 6,379,333 B1 | 4/2002 | Brimhall et al. |
| 6,443,929 B1 | 9/2002 | Kuracina |
| 6,595,955 B2 | 7/2003 | Ferguson et al. |
| 6,629,959 B2 | 10/2003 | Kuracina et al. |
| 6,659,984 B2 | 12/2003 | Crawford et al. |
| 6,689,102 B2 | 2/2004 | Greene |
| 6,695,814 B2 | 2/2004 | Greene et al. |
| 6,743,186 B2 | 6/2004 | Crawford et al. |
| 6,749,588 B1 | 6/2004 | Howell et al. |
| 6,761,706 B2 | 7/2004 | Vaillancourt |
| 6,786,891 B2 | 9/2004 | Hiejima |
| 6,860,871 B2 | 3/2005 | Kuracina et al. |
| 6,881,202 B2 | 4/2005 | Coleman et al. |
| 6,976,976 B2 | 12/2005 | Doyle |
| RE38,996 E | 2/2006 | Crawford et al. |
| 6,997,902 B2 | 2/2006 | Thorne et al. |
| 7,125,397 B2 | 10/2006 | Woehr et al. |
| 7,144,387 B2 | 12/2006 | Millerd |
| 7,264,613 B2 | 9/2007 | Woehr et al. |
| 7,303,548 B2 | 12/2007 | Rhad et al. |
| 7,322,963 B2 | 1/2008 | Goh |
| 7,387,616 B2 | 6/2008 | Li |
| 7,611,499 B2 | 11/2009 | Woehr et al. |
| 7,811,261 B2 | 10/2010 | Rubinstein et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 8,100,858 B2 | 1/2012 | Woehr et al. |
| 8,235,945 B2 | 8/2012 | Baid |
| 8,251,950 B2 | 8/2012 | Albert et al. |
| 8,545,454 B2 | 10/2013 | Kuracina et al. |
| 8,556,853 B2 | 10/2013 | Vaillancourt et al. |
| 2001/0047156 A1 | 11/2001 | Parker |
| 2002/0111566 A1 | 8/2002 | Crawford et al. |
| 2003/0036731 A1 | 2/2003 | Wilkinson et al. |
| 2003/0105431 A1 | 6/2003 | Howell |
| 2003/0216687 A1 | 11/2003 | Hwang |
| 2003/0220587 A1 | 11/2003 | Swenson |
| 2004/0049155 A1 | 3/2004 | Schramm |
| 2004/0049163 A1 | 3/2004 | Murashita |
| 2004/0167385 A1 | 8/2004 | Rioux et al. |
| 2004/0225262 A1 | 11/2004 | Fathallah et al. |
| 2005/0015054 A1 | 1/2005 | Chen |
| 2005/0119627 A1 | 6/2005 | Crawford |
| 2007/0100297 A1 | 5/2007 | Woehr et al. |
| 2008/0171986 A1 | 7/2008 | Baid |
| 2009/0131876 A1 | 5/2009 | Coyne |
| 2010/0016804 A1 | 1/2010 | Muskatello et al. |
| 2010/0191188 A1 | 7/2010 | Harding et al. |
| 2010/0191189 A1 | 7/2010 | Harding et al. |
| 2010/0249707 A1 | 9/2010 | Woehr et al. |

FOREIGN PATENT DOCUMENTS

| | | |
|---|---|---|
| DE | 3808353 A1 | 8/1989 |
| EP | 0443735 A1 | 8/1991 |
| EP | 0747085 A2 | 12/1996 |
| EP | 0749761 A1 | 12/1996 |
| EP | 0750916 A2 | 1/1997 |
| EP | 0826388 A2 | 3/1998 |
| EP | 0995459 A2 | 4/2000 |
| EP | 1291035 A2 | 3/2003 |
| EP | 1369142 B1 | 8/2005 |
| EP | 2016964 A1 | 1/2009 |
| EP | 2075029 A1 | 7/2009 |
| FR | 2767480 A1 | 2/1999 |
| JP | H04102462 A | 4/1992 |
| JP | 2002330946 A | 11/2002 |
| JP | 2002539897 T | 11/2002 |
| WO | 9211885 A1 | 7/1992 |
| WO | 0057940 A1 | 10/2000 |
| WO | 0156642 A1 | 8/2001 |
| WO | 03011381 A1 | 2/2003 |
| WO | 2004043521 A1 | 5/2004 |
| WO | 2006096634 A1 | 9/2006 |
| WO | 2006096635 A1 | 9/2006 |
| WO | 2006096636 A1 | 9/2006 |
| WO | 2007022373 A2 | 2/2007 |
| WO | 2010101573 A1 | 9/2010 |

(56) References Cited

FOREIGN PATENT DOCUMENTS

| WO | 2010110789 A1 | 9/2010 |
|---|---|---|
| WO | 2012075402 A1 | 6/2012 |
| WO | 2012075421 A1 | 6/2012 |

OTHER PUBLICATIONS

Erskine, Canadian Application No. 2,599,945, Notice of Allowance dated Nov. 15, 2010, 1 pages.
Erskine, Canadian Application No. 2,599,955, Office Action dated Dec. 21, 2010, 3 pages.
Erskine, Canadian Application No. 2,599,938, Office Action dated Dec. 20, 2010, 2 pages.
Erskine, Japanese Application No. P2008-500805, Final Office Action dated Jan. 25, 2011, 25 pages.
Erskine, Japanese Application No. P2008-500804, Notice to Grant dated Feb. 2, 2011, 6 pages.
Erskine, Office Communication for Application No. 11/817,687 dated Dec. 9, 2010, 19 pages.
Erskine, Mexican Application No. MX/a/2007/010944, Office Action dated Mar. 11, 2011, 4 pages.
European Patent Application No. EP06737125, Search Report dated Feb. 10, 2010.
Erskine, Australian IP Examination Report No. 2 dated Feb. 25, 2010, Reference No. 30355386/MRF/TLG/tzs, Application No. 2006220690, 2 pages.
Erskine, Canadian Application No. 2,599,943, Office Action dated Nov. 20, 2009, 2 pages.
Erskine, Chinese Application No. 200680007590, Office Action dated Aug. 21, 2010, 4 pages.
Erskine, Australian Application No. 2006220691, Notice of Acceptance dated Jun. 9, 2010, 2 pages.
Erskine, Canadian Application No. 2,599,945, Office Action dated Nov. 13, 2009, 2 pages.
Erskine, Chinese Application No. 200680007484, Notification to Grant Patent Right dated Jun. 11, 2010, 4 pages.
Patent Cooperation Treaty, PCT/US06/07911, PCT International Search Report and Written Opinion, dated Jun. 23, 2006, 8 pages.
Patent Cooperation Treaty, PCT/US06/07911, PCT International Preliminary Report on Patentability, dated Feb. 12, 2007, 4 pages.
Erskine, U.S. Appl. No. 11/817,891, Office Communication dated Jun. 11, 2010, 11 pages.
Erskine, Australian Application No. 2006220692, Examiners First Report on Patent Application dated Oct. 21, 2008, 2 pages.
Erskine, Canadian Application No. 2,599,955, Office Action dated Mar. 5, 2010, 2 pages.
Erskine, Chinese Application No. 200680007485.0, Office Action dated Jun. 19, 2009, 6 pages.
Erskine, Chinese Application No. 200680007485.0, Notification to Grant Patent Right dated Jun. 4, 2010, 5 pages.
Erskine, Japanese Application No. P2008-500805, Office Action dated Apr. 20, 2010, 4 pages.
Erskine, Malaysia Application No. PI 20071465, Substantive Examination Report dated Apr. 30, 2010, 3 pages.
Patent Cooperation Treaty, PCT/US06/07912, PCT International Preliminary Report on Patentability, dated Sep. 20, 2007, 5 pages.
Patent Cooperation Treaty, PCT/US06/07912, PCT International Search Report and Written Opinion, dated Jun. 26, 2006, 8 pages.
Erskine, Taiwanese Application No. 095107584, Decision to Grant Patent dated Mar. 4, 2009, 5 pages.
Erskine, U.S. Appl. No. 11/817,687, Office Communication dated Jun. 30, 2010, 8 pages.
Erskine, U.S. Appl. No. 11/817,687, Office Communication dated Jan. 21, 2010, 9 pages.
Erskine, Australian Application No. 2006220689, Examiners First Report on Patent Application dated Jan. 15, 2009, 3 pages.
Erskine, Australian Application No. 2006220689, Patent Granted dated Jun. 18, 2010, 3 pages.
Erskine, Canadian Application No. 2,599,938, Office Action dated Feb. 23, 2010, 2 pages.
Erskine, Chinese Application No. 20068007548.2, Office Action dated Sep. 4, 2009, 4 pages.
Erskine, Chinese Application No. 200680007548.2, Notification to Grant Patent Right dated Jun. 12, 2010, 4 pages.
Erskine, Australian Application No. 2006220690, Notice of Acceptance dated Jun. 15, 2010, 3 pages.
Erskine, Japanese Application No. P2008-500802, Office Action dated Jun. 29, 2010, 6 pages.
Erskine, Malaysia Application No. PI 20071468, Substantive Examination Report dated Apr. 16, 2010, 2 pages.
Patent Cooperation Treaty, PCT/US06/07910, PCT International Preliminary Report on Patentability, dated Jul. 3, 2007, 20 pages.
Patent Cooperation Treaty, PCT/US06/07909, PCT International Search Report and Written Opinion, dated Jun. 26, 2006, 8 pages.
Erskine, Taiwanese Application No. 095107593, Decision to Grant Patent dated Dec. 11, 2009, 5 pages.
Patent Cooperation Treaty, PCT/US09/036197, PCT International Search Report and Written Opinion dated Apr. 28, 2009, 14 pages.
Patent Cooperation Treaty, PCT/US09/038246, PCT International Search Report and Written Opinion dated May 20, 2009, 11 pages.
Erskine, U.S. Appl. No. 11/817,891, Office Communication dated Oct. 19, 2009, 10 pages.
Erskine, Australian Application No. 2006220690, Examiner's First Report on Patent dated Nov. 11, 2008, 3 pages.
Erskine, Chinese Application No. 200680007590, Office Action dated May 21, 2009, 11 pages.
Erskine, European Application No. EP06737126, Supplementary European Search Report dated Feb. 11, 2010, 4 pages.
Patent Cooperation Treaty, PCT/US06/07910, PCT International Search Report and Written Opinion, dated Jul. 5, 2006, 8 pages.
Erskine, Taiwanese Application No. 095107587, Office Action dated Oct. 12, 2009, 12 pages.
Erskine, Australian Application No. 2006220691, Examiner's First Report on Patent dated Sep. 19, 2009, 2 pages.
Erskine, Chinese Application No. 200680007484, Office Action dated Aug. 21, 2009, 13 pages.
Erskine, Taiwanese Application No. 095107585, Office Action dated Apr. 6, 2009, 9 pages.
Erskine, Taiwanese Application No. 095107585, Office Action dated Oct. 15, 2009, 7 pages.
Osinski, U.S. Appl. No. 11/817,687, Notice of Allowance & Fees Due, Jun. 30, 2011, 8 pages.
Erskine, Japanese Application No. JP07-5616-XY, Decision to Grant a Patent, dated Apr. 5, 2011, 6 pages.
Erskine, Taiwan Application No. 095107585, Office Action, dated Mar. 17, 2011, 3 pages.
Erskine, Mexian Application No. MX/a/2007/010946, Office Action, dated Apr. 2011, 2 pages.
Erskine, Japan Application No. P2008-500802, Notice of Reasons for Rejection, dated Apr. 5, 2011, 4 pages.
Erskine, China Application No. 201010109122.6, Office Action, dated Apr. 1, 2011, 11 pages.
Price, Office Action Communication for U.S. Appl. No. 11/817,890 dated Aug. 31, 2011, 33 pages.
Patent Cooperation Treaty, International Preliminary Report on Patentability and Written Opinion of the International Searching Authority for PCT/US2009/038246 dated Oct. 6, 2011, 7 pages.
Patent Cooperation Treaty, International Preliminary Report on Patentability and Written Opinion of the International Searching Authority for PCT/US2009/036197 dated Sep. 15, 2011, 10 pages.
Patent Cooperation Treaty, Notification of Transmittal of the International Search Report and the Written Opinion of the International Searching Authority, or the Declaration for PCT/US2011/063118 dated Apr. 3, 2012, 17 pages.
Patent Cooperation Treaty, Notification of Transmittal of the International Search Report and the Written Opinion of the International Searching Authority, or the Declaration for PCT/US2011/063081 dated Mar. 22, 2012, 10 pages.
Desanto, Office Action Communication for U.S. Appl. No. 11/817,890 dated Apr. 30, 2012, 14 pages.
Shamsudin, Substantive/Modified Substantive Examination and Search Report, Application No. PI 20071467, Mar. 15, 2013, 4 pages.

(56) References Cited

OTHER PUBLICATIONS

Ehrsam, Supplementary European Search Report, Application No. EP 09 84 1250, Feb. 26, 2013, 5 pages.
Omgba, Office Action Correspondence, U.S. Appl. No. 13/114,589, Apr. 10, 2013, 15 pages.
Patent Cooperation Treaty, Notification of Transmittal of the International Search Report and the Written Opinion of the International Searching Authority, or the Declaration for PCT/US12/32578 dated Aug. 3, 2012, 26 pages.
European Patent Office, European Search Report for EP12169737 dated Jul. 25, 2012, 4 pages.
European Patent Office, European Search Report for EP12169713 dated Jul. 26, 2012, 5 pages.
Price, U.S. Appl. No. 11/817,891, Non-Final Office Action, Sep. 16, 2014, 94 pgs.
European Patent Office, Supplementary European Search Report for EP09842422 dated Aug. 27, 2012, 7 pages.
Desanto, Office Action Communication for U.S. Appl. No. 11/817,890 dated Oct. 11, 2012, 26 pages.
Desanto, Notice of Allowance and Fee(s) Due for U.S. Appl. No. 11/817,890 dated Sep. 17, 2013, 17 pages.
Matney, Office Action Communication for U.S. Appl. No. 13/254,163 dated Oct. 15, 2013, 81 pages.
Omgba, Office Action Communication for U.S. Appl. No. 13/144,589 dated Oct. 31, 2013, 19 pages.
Patent Cooperation Treaty, Preliminary Report on Patentability and Written Opinion of the International Searching Authority for PCT/US2012/032578 dated Oct. 8, 2013, 10 pages.
European Patent Office, Intention to Grant for EP Application No. 06 737 126.0 dated Jun. 17, 2013, 92 pages.
Canadian Patent Office, Notice of Allowance for CA Application No. 2,599,943 dated Jul. 3, 2013, 1 page.
Desanto, Office Action Communication for U.S. Appl. No. 11/817,890 dated Jun. 6, 2013, 19 pages.
Patent Cooperation Treaty, International Preliminary Report on Patentability for PCT/US20111063081 dated Jun. 4, 2013, 7 pages.
Patent Cooperation Treaty, International Preliminary Report on Patentability for PCT/US2011/063118 dated Jun. 4, 2013, 8 pages.
Omgba, Office Action Communication for U.S. Appl. No. 13/114,589 dated Sep. 14, 2012, 39 pages.
Flick: U.S. Appl. No. 13/259,715 filed Dec. 2, 2011, Office Action Dec. 17, 2012, 42pgs.
State Intellectual Property Office of the the People's Republic of China, Notification of the First Office Action for Application No. CN 201180066317 dated Oct. 27, 2014, 19 pages.

\* cited by examiner

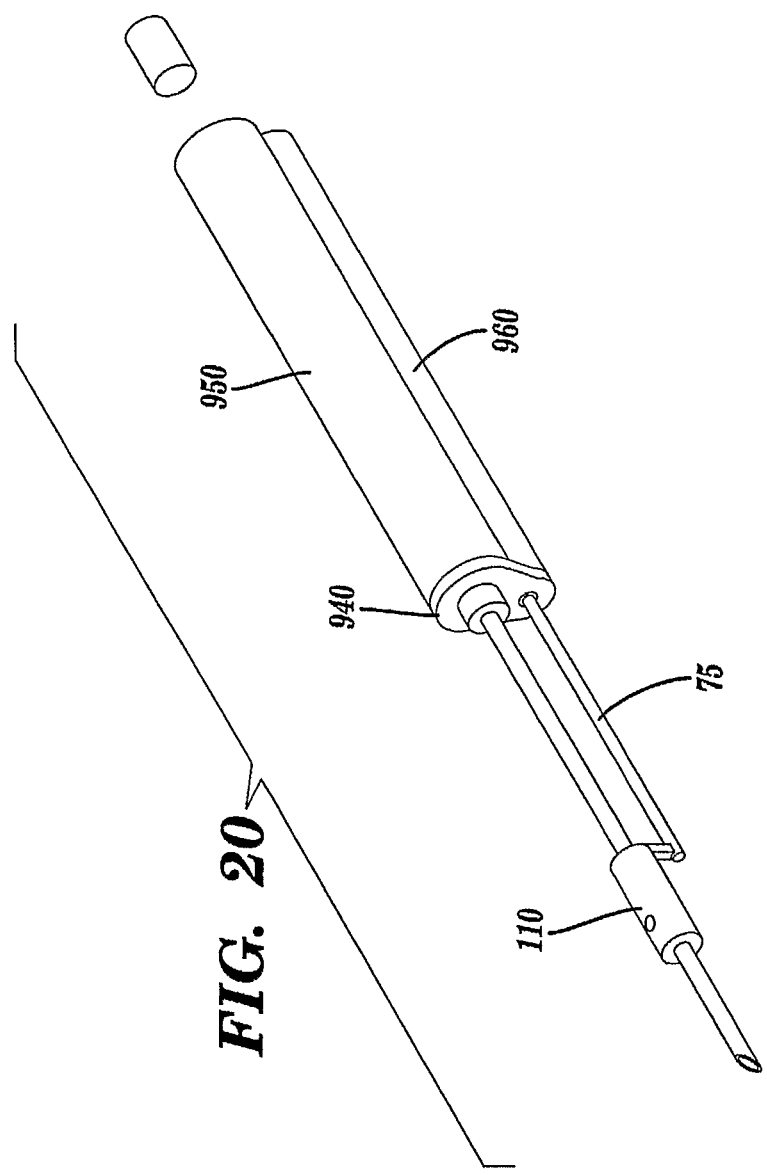

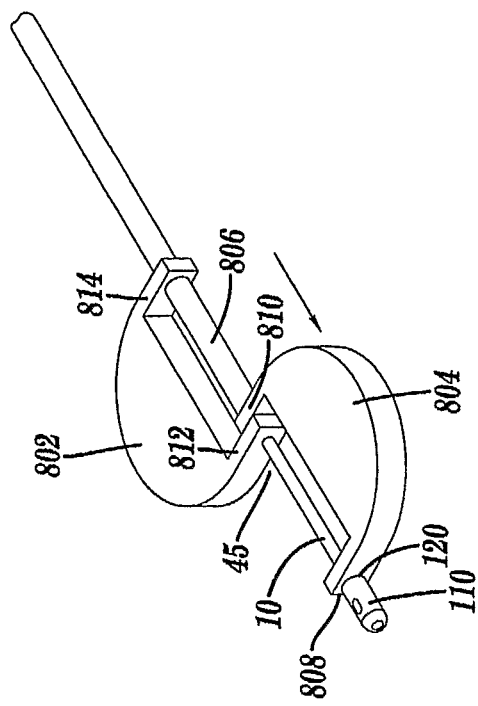
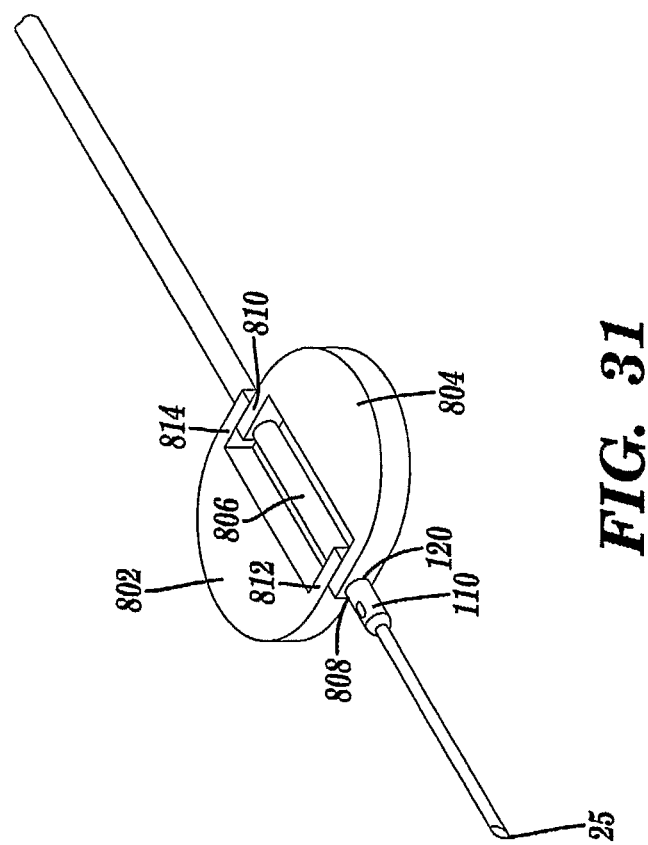

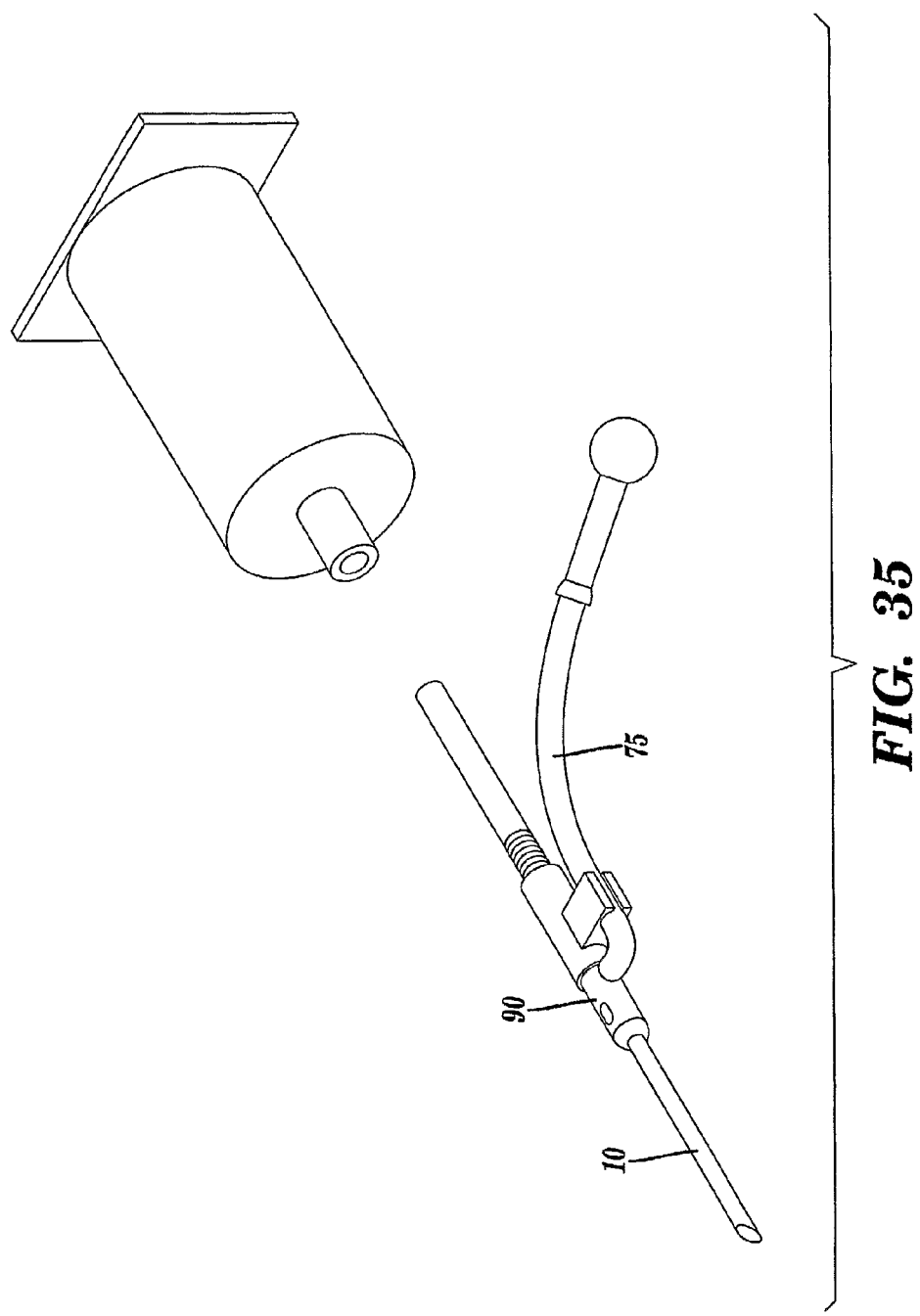

METHOD OF MAKING A NEEDLE SHIELDING DEVICE

CROSS-REFERENCE TO RELATED APPLICATIONS

This patent application claims priority from, and expressly incorporates by reference, the following provisional patent applications:

60/659,226—Shielding Apparatus for Locking onto a Needle—filed on Mar. 7, 2005;
60/659,217—Needle Shielding Apparatus with Tubular Needle Cover—filed on Mar. 7, 2005;
60/659,213—Needle Shielding Apparatus with Tether to Needle Hub—filed on Mar. 7, 2005;
60/714,954—Blood Collection Device with Needle Shield—filed on Sep. 7, 2005.

BACKGROUND

This patent application relates to medical devices using needles such as spinal needles, intravenous catheter introducers, blood collection devices and syringes. It includes methods of manufacturing needle based devices and needle shields for such devices.

SUMMARY OF THE INVENTION

The invention includes a method of making a needle assembly. The needle has a proximal end, a sharp distal end and a longitudinal axis. A needle shield assembly is provided with a blocking object carrier, a blocking object (preferably a ball) and a lumen coaxial with the longitudinal axis of the needle. The lumen has a proximal end and a distal end. The blocking object is moveable from a shielding position in which the blocking object at least partially occludes the lumen and a non-shielding position in which the needle can slide along the lumen. The blocking object is placed in the blocking object carrier in the shielding position. The proximal end of the needle is inserted into the distal end of the lumen and the needle shield assembly is moved such that the needle moves the blocking object from the shielding position to a non-shielding position.

A spring is attached to the blocking object carrier such that the spring biases the blocking object towards the longitudinal axis of the needle. If the device is a catheter introducer assembly then a catheter tube is threaded over the needle. A catheter adapter is snapped onto the needle shield assembly. At least part of the needle shield assembly is placed inside a catheter adapter. The blocking object is preferably a ball, but may be a non-spherical object such as a roller.

The blocking object carrier preferably holds the blocking object in a position offset from the longitudinal axis of the needle in the shielding position. At least part of the needle shield assembly is placed inside a catheter adapter.

A method of manufacturing a catheter introducer assembly is also disclosed. A polymeric tube is extruded and attached to a needle hub such that it slides relative to the needle hub. A catheter assembly is placed on the needle. In a further method of the invention, a second polymeric tube is extruded and secured to the needle hub. The first and second polymeric tubes are concentric. The step of extruding the polymeric tube may include providing reinforcing in the polymeric tube. The polymeric tube and the reinforcing may be coextruded.

Another method involves extruding a polymeric tube, securing a needle hub and a needle to the distal end of the polymeric tube and placing a catheter assembly on the needle. The polymeric tube may have a second, substantially parallel polymeric tube such that the polymeric tube comprises more than one lumen.

These and other features of the invention are described in greater detail below.

BRIEF DESCRIPTION OF THE DRAWINGS

FIG. 20 is an isometric view of a catheter introducer with a needle shield in which the shield housing is made from an extruded polymeric tube;

FIGS. 31-32 are isometric views of winged catheter introducers equipped with the needle shield;

FIG. 35 is an isometric view of a blood collection device with the needle shield;

DETAILED DESCRIPTION

The following is a description of embodiments of the invention as applied to catheter introducers, a syringes and other needle based devices. It is not intended to limit the scope of the invention.

The invention may be applied to a wide variety of needle based devices such as catheter introducers, syringes, winged needles and Huber needles. In almost all cases, shielding a needle involves providing a needle shield and ensuring that it does not come off the sharp distal end of the needle or move proximally, thereby re-exposing the sharp distal end. Some sort of locking mechanism or mechanisms must therefore prevent distal and proximal movement of the shield once the needle is shielded.

Figure 1A:
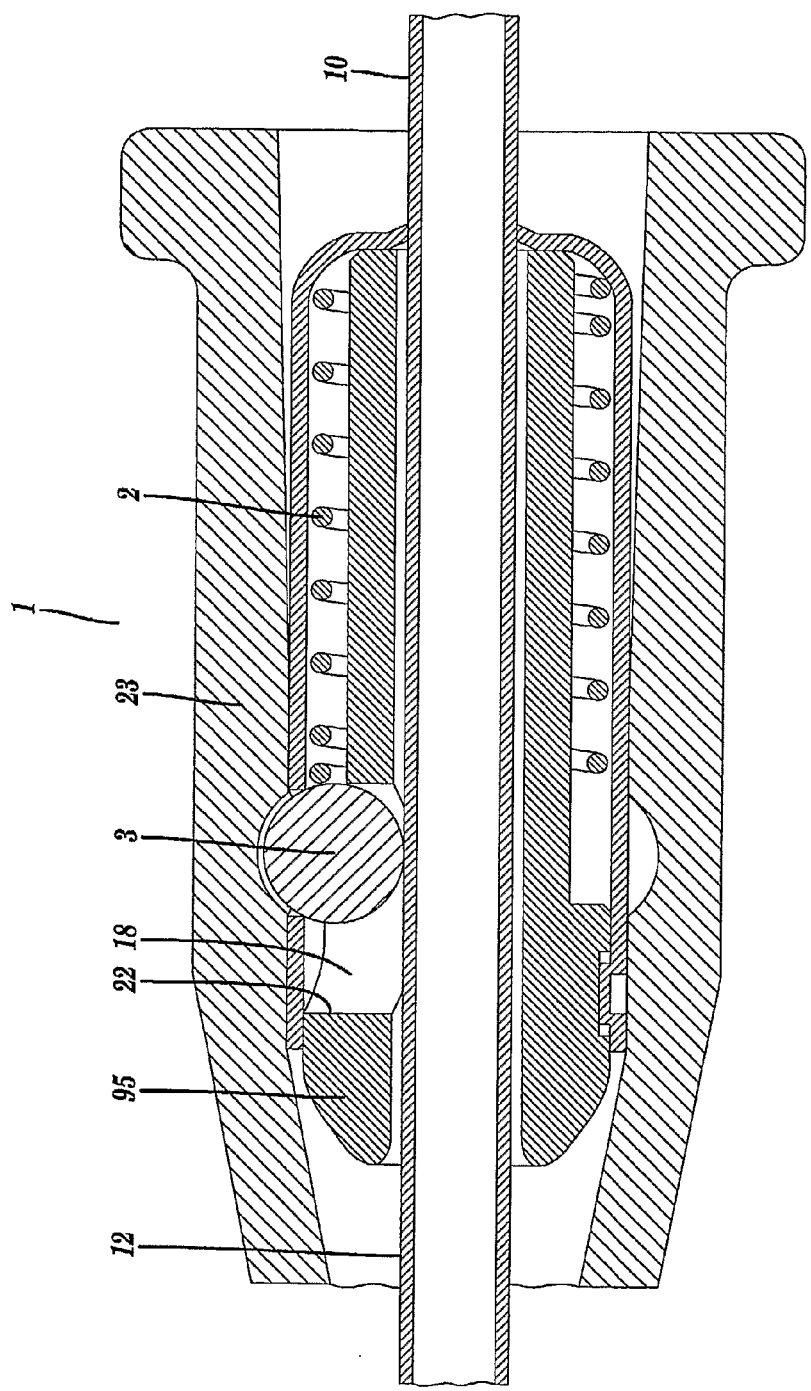
FIGS. 1A, B and C are cross-sectional views showing an embodiment of the invention as applied to a catheter introducer.
Figure 1B:
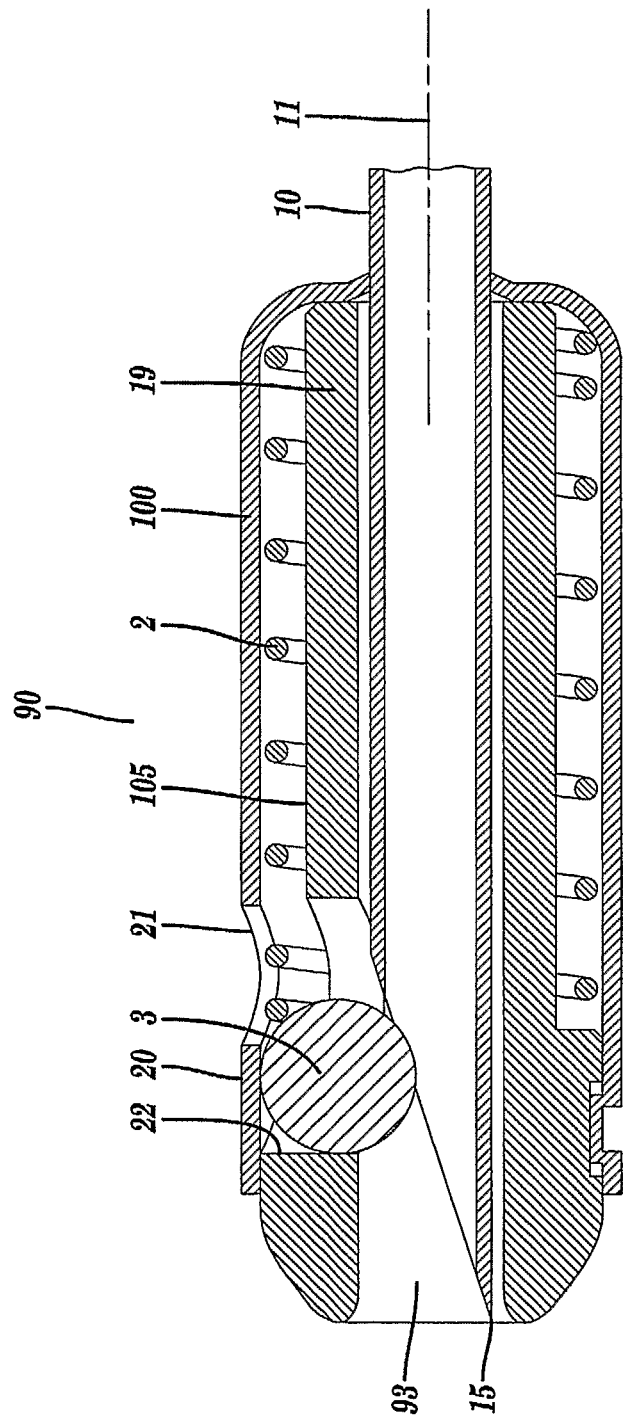
Figure 1C:
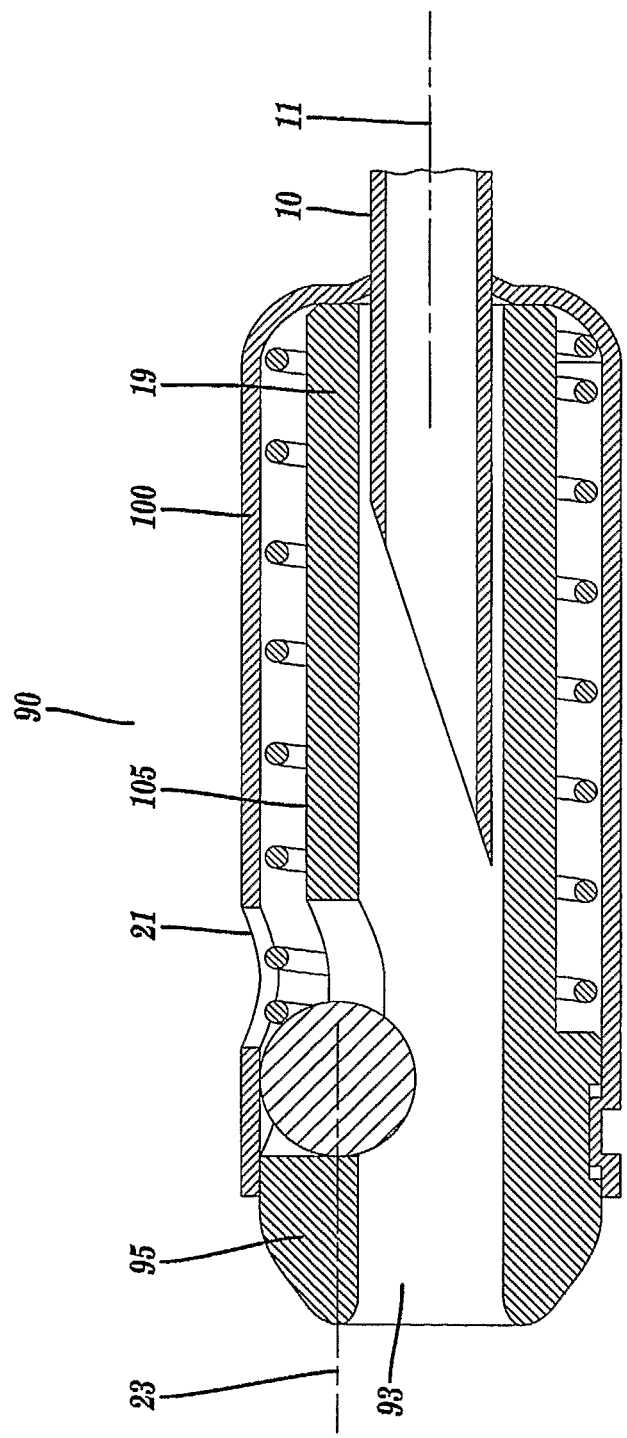
Figure 2:
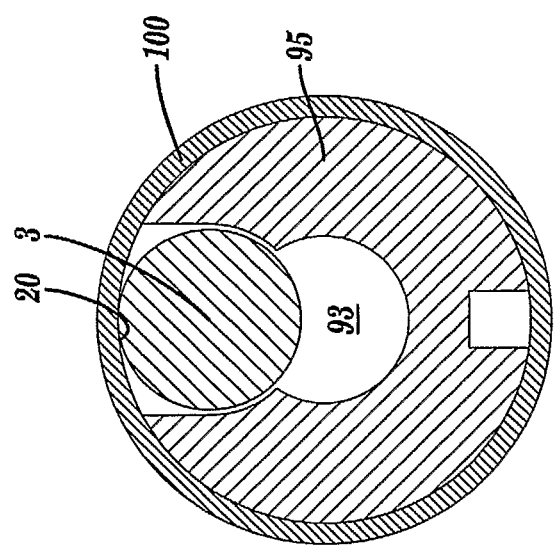
FIG. 2 is a cross sectional view through the needle shield in a deployed position.
Figure 4:
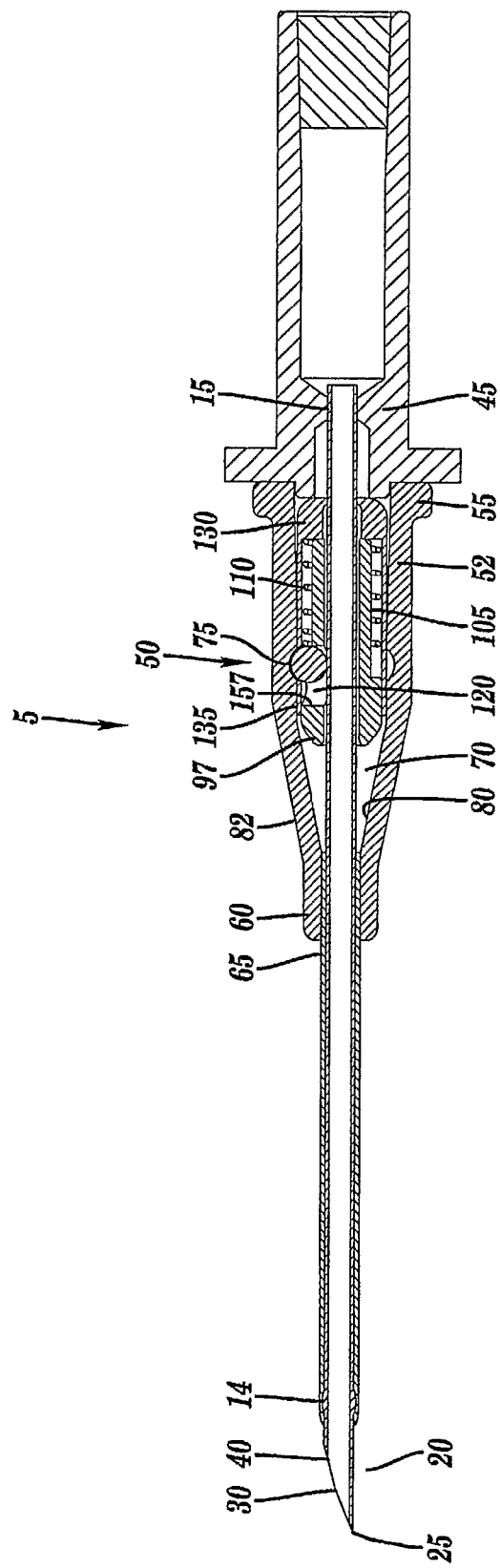
FIG. 4 is an orthogonal cross-sectional view through a catheter introducer assembly with the needle shield in a non-deployed position.

In the present invention, proximal movement of the shield is prevented by the assembly shown in FIGS. 1A, B and C and FIG. 2. Assembly 1 comprises needle 10, having a longitudinal axis 11, an outer surface 12 and a sharp distal end 15. Needle shield assembly 90 has an internal lumen 93, which is coaxial with needle 10. Needle shield assembly 90 is shown inside a catheter adapter or hub 23 in FIG. 1A. Shield assembly 90 is made up of a first housing 95 which is covered with a cap 100. First housing 95 has a stepped area or area of reduced diameter 105 onto which spring 2 is threaded. First housing 95 has an opening 18 which with first housing 95 forms a holder or carrier 16 (as shown in FIGS. 1A and 4) for ball 3. Opening 18 extends from outer wall 19 through to lumen 93. Opening 18 is configured such that ball 3 can move in it but the movement of ball 3 is restricted radially, longitudinally and circumferentially relative to axis 11.

In the non-shielding position shown in FIG. 1A, ball 3 protrudes through hole 21 in cap 100. Spring 2 exerts a force on ball 3 which has an axial component and a component radially towards axis 11. In the non-shielding position, ball 3 touches outer surface 12 of needle 10. The biasing force of spring 2 thus makes ball 3 tend towards axis 11.

As shield assembly 90 slides along needle 10, it approaches distal end 15. The biasing force in spring 2 forces ball 3 at least partially into lumen 93 and it leaves hole 21 and moves radially towards axis 11 in opening 18, as the bevel of needle 10 passes ball 3. Due to the geometry of opening 18, when the bevel has passed by, ball 3 lies at least partially in lumen 93. Axis 24 of ball 3 lies offset from axis 11. Radial movement of ball 3 is restricted by spring 2 and by top wall 20 of cap 100.

Axial movement of the ball is also restricted by front wall 22 of opening 18. Distal movement of needle 10 forces ball 3 against wall 22. If shield 90 now slides proximally (i.e. needle 10 slides distally), needle 10 will be blocked by ball 3, which lies at least partially in lumen 15 and movement of which is limited by spring 2 and walls 20 and 22.

Figure 3:
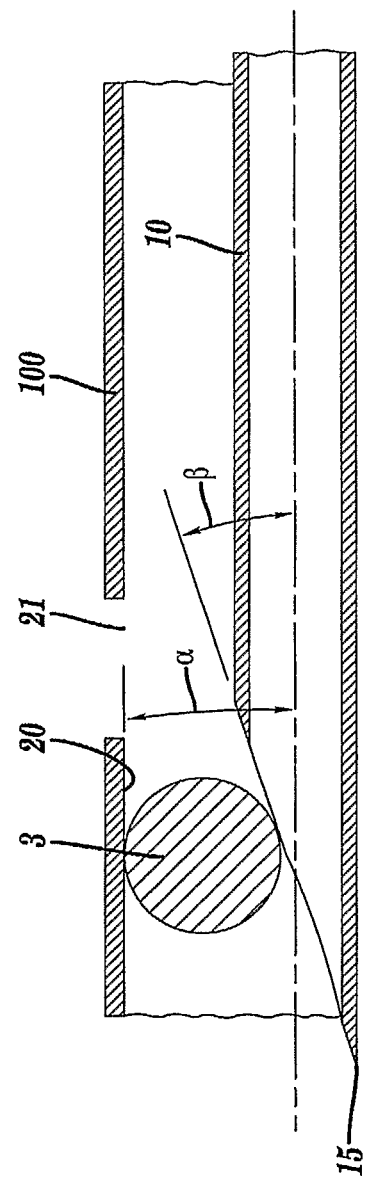
FIG. 3 is an orthogonal cross-sectional view showing the angles between needle bevel and shield wall.

Referring to FIG. 3, wall 20 of cap 100 forms an angle α tangential to ball 3 when ball 3 is moving into its position at least partially occluding lumen 93. This angle α is set at a value less than the smallest bevel angle of needle tip 15. In the embodiment described here, the angle α between wall 20 and ball 3 is about zero degrees. If that angle is made too large relative to angle, ball 3 will not be trapped.

The above operation is described in greater detail and with slight variations in the remainder of this specification in the context of catheter introducers, syringes and other needle-based medical devices. Three types of catheter introducer are shown. In the first, distal movement of the needle shield off the sharp end of the needle is restrained by means of an abutment between the needle shield and a discontinuity on the introducer needle. In the second, the needle shield is on the end of a tubular member, distal movement of which is restrained by an abutment with a member attached to the needle hub. In the third, the needle shield is tethered to the needle hub, thereby preventing distal movement of the needle shield off the sharp end of the needle. The same applies to the syringe. In all cases, proximal movement and hence pulling back of the needle to expose the sharp end of the needle, is prevented by the device described above.

The following is a description of the invention as applied to a first type of catheter introducer assembly in which distal movement of the needle shield assembly is restrained by a discontinuity on the needle such as a bump or crimp. Reference is made to FIGS. 4-8.

The purpose of catheter introducer assembly 5 is to pierce a human or animal body with a needle, make an opening, insert a catheter tube into it and then remove the needle. In order to prevent the spread of infectious disease through needle sticks, the tip of the needle should be shielded once it is removed.

The body is pierced by needle 10, which has an outer surface 12, a proximal end 15, a distal end 20 and a lumen 22. Distal end 20 has a sharp tip or point 25. Distal end is beveled. In the drawings it is shown with two bevels—surfaces 30 and 40 forming a slope extending from the sharp point 25 in a proximal direction. More or less than two bevels may be used. Proximal end 15 is secured to needle hub 45. Needle 10 has an area of enlarged cross section 14 located close to distal end 20. This enlarged cross section can be in the form of an annular ring, enlarging the diameter of needle 10, a segmented ring or a discontinuity, bump or crimp on the needle. The enlarged cross section can be formed on needle 10 by crimping, grinding, deforming or depositing material on the surface of the needle. The difference between the diameter of needle 10 and this enlarged cross section is very small—about 0.004 inches—and its length is only about 0.03 inches.

Catheter assembly 50 has a catheter hub 52 having proximal end 55, distal end 60 and lumen 70 extending between the proximal and distal ends. Catheter tube 65 extends distally out of distal end 60. Needle 10 lies within lumen 70 of catheter assembly 50 prior to insertion into the body. Once needle 10 has been inserted into the patient, together with catheter tube 65, needle 10 is withdrawn by pulling it in a proximal direction. Catheter hub 52 has an inner surface 80 and an outer surface 82. Inner surface 80 is provided with a circumferential groove 75, the purpose of which will be explained in due course. A single depression, indentation, circumferential ridge or raised portion will serve the same purpose as the circumferential groove.

Needle shield assembly 90 is contained in two mating parts—first housing 95 and second housing or cap 100. Needle assembly housing 90 can fit within catheter hub 50. First housing 95 has a distal end 97 and a proximal end 99. Extending between the proximal and distal ends is lumen 93, which is dimensioned so that first housing 95 can slide axially and rotate on needle 10. Extending from near distal end 97 towards proximal end 99 is stepped area 105. This is an area of reduced diameter which allows coil spring 110 to be placed on first housing 95. Spring 110 is a compression spring, which exerts a force axially in the proximal and distal directions. Other types of springs can be used, for example, a leaf spring (see FIG. 41) or a wave spring washer (see FIG. 42).

Towards distal end 97 of first housing 95, but still in the stepped area 105, first housing 95 is provided with an opening 120, dimensioned to accommodate ball 122. Second housing or cap 100 has a proximal end 130 and a distal end 135. Proximal end 130 is provided with opening 140 which is dimensioned such that it is slightly larger than the diameter of needle 10, but slightly smaller than the diameter of area of enlarged cross section 14. Thus, second housing can slide axially along the needle from proximal end 15 towards distal end 20, until its opening 140 abuts area of enlarged cross section 14, at which time it cannot slide further in the distal direction. When first and second housings 95 and 100 are assembled, second housing 100 covers most of first housing 95, except for distal end 97 of the first housing. Second housing 100 thus covers spring 110. Second housing 100 is provided with opening 150 which is dimensioned such that part of ball 122 can protrude through it and into groove 75.

When needle shield assembly 90 is in catheter hub 52, prior to deployment, part of ball 122 protrudes through opening 150 and lies in groove 75. This locks needle shield assembly 90 to catheter hub 52, while allowing catheter hub 52 to rotate relative to needle shield assembly 90, depending on the extent of groove 75 (i.e. whether it is circumferential or permits only limited movement because it does not extend around the entire inner circumference of the catheter hub). Part of ball 122 also lies in lumen 93 of first housing 95 and abuts outer surface 12 of needle 10 (i.e. ball 122 touches outer wall 12 of needle 10). Needle 10 and shield assembly 90 can slide and rotate relative to each other with very low friction. Ball 122 is radially constrained by groove 75 and needle 10. Needle shield assembly 90 is thus locked into catheter hub 52. Spring 110 exerts a force on ball 122 axially, in the distal direction. Moreover, the presence of needle 10 abutting ball 122 radially constrains ball 122 and prevents it from moving out of groove 75.

Once catheter tube 65 has been placed in the patient, needle 10 is pulled in a proximal direction (that is to say, as needle shield assembly 90 moves towards tip 25 of needle 10). If first bevels 30 and 40 are facing ball 122, then, when first bevel 40 comes into alignment with ball 122, ball 122 is less radially constrained by needle 10 and, urged by spring 110, it begins to move in opening 120, distally and radially. Ball 122 thus moves out of opening 150 and groove 75 and radially inwards further into lumen 93 of shield assembly 90, pivoting about edge 155, (a wall of opening 150 in second housing 100) and sliding distally along the length of opening 120. As needle 10 continues its proximal movement, it no longer constrains it radially and ball 122 moves completely out of groove 75. When ball 122 is positioned such that edge 155 is above it, ball 122 will have traveled radially into lumen 93 as far as it can, constrained by the dimensions of opening 120 and partially occluding lumen 93.

If bevels 30 and 40 are not facing ball 122 or are partially facing ball 122, the device operates in a similar manner. That is to say, when needle tip 25 passes ball 122, needle 10 no longer constrains ball 122. Spring 110 urges ball 122 along opening 120 so that ball 122 moves out of groove 75 and pivots about edge 155. Ball 122 is constrained from entering lumen 93 by the dimensions and geometry of opening 120. Ball 122 thus partially occludes lumen 93.

Figure 5:
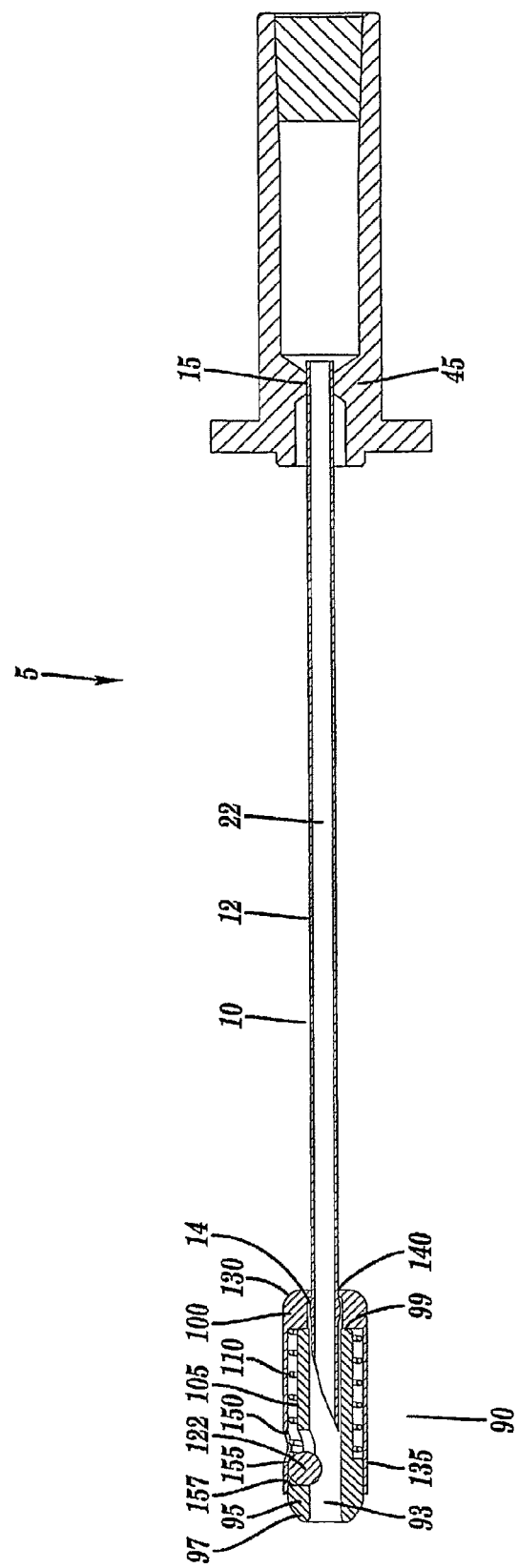
FIG. 5 is an orthogonal cross-sectional view through a catheter introducer assembly with the needle shield in a deployed position.
Figure 7:
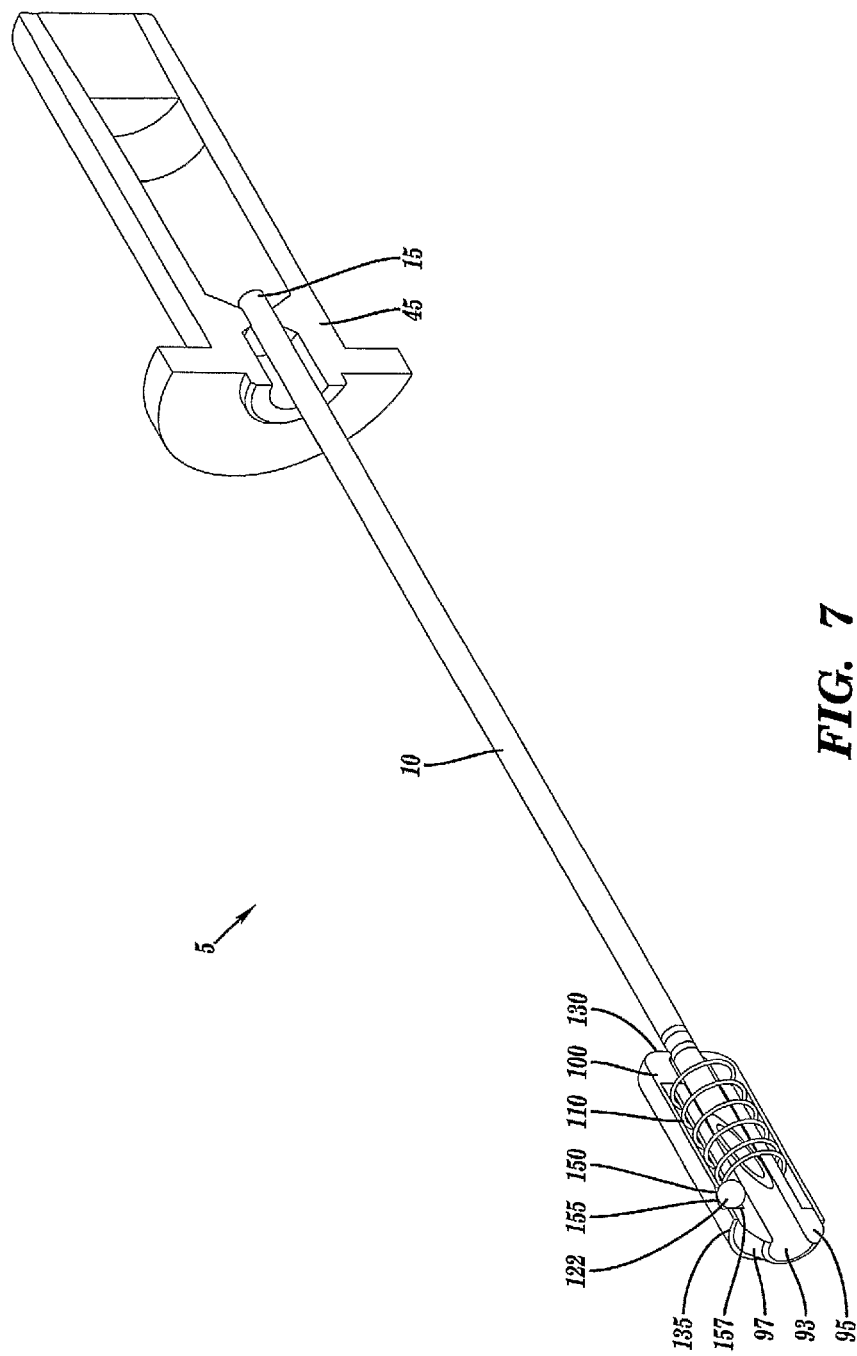
FIG. 7 is an isometric cross-sectional view through a catheter introducer assembly with 15 the needle shield in a deployed position.
Figure 8:
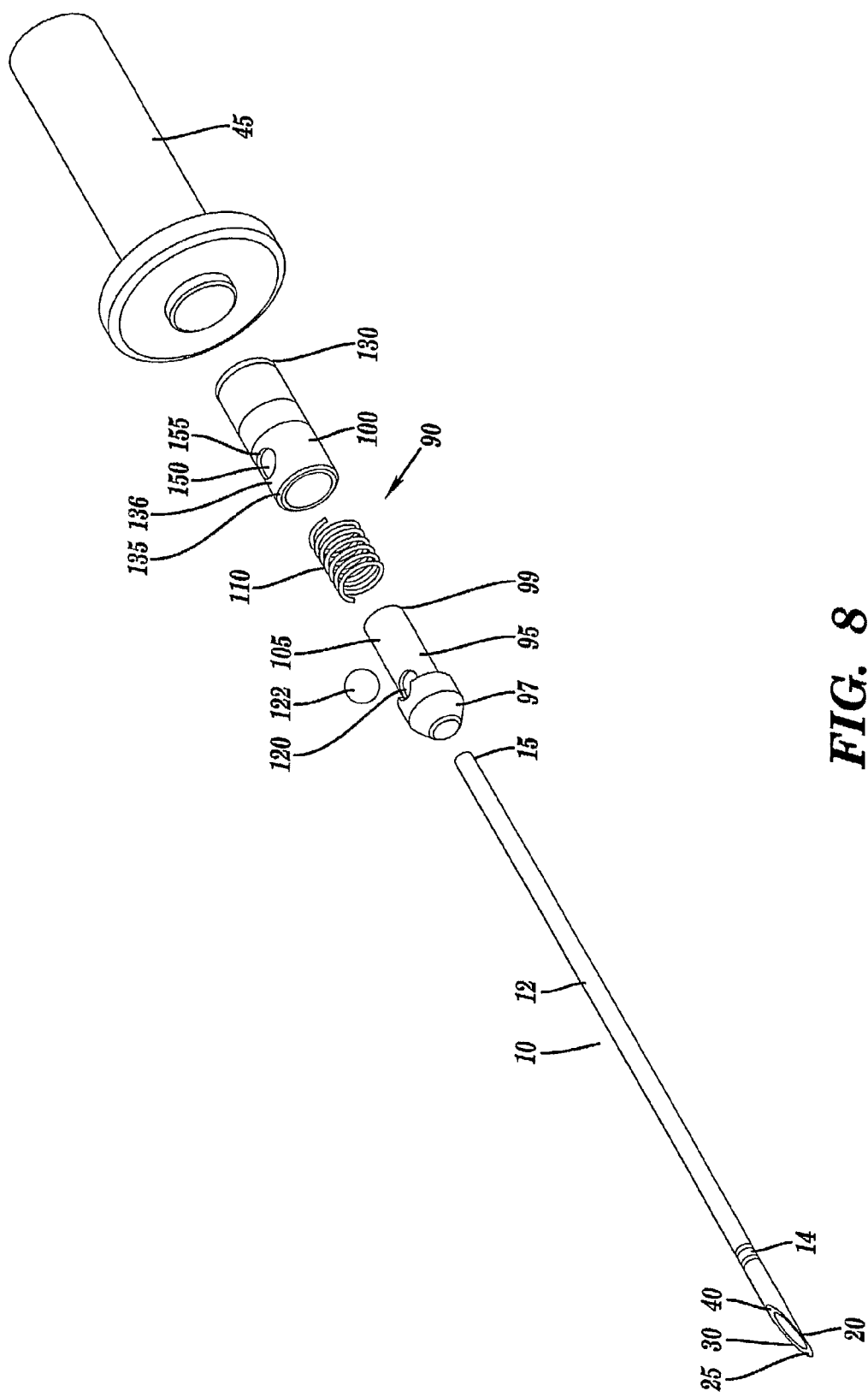
FIG. 8 is an exploded view of the components of the needle shielding device and the needle hub.
Figure 9:
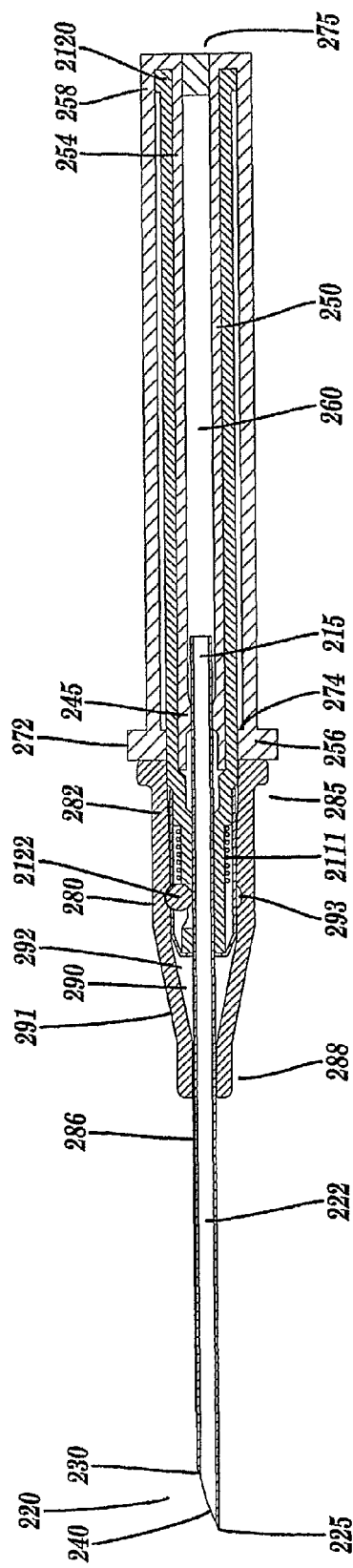
FIG. 9 is an orthogonal cross-sectional view through a catheter introducer assembly with the needle shield in a non-deployed position.
Figure 10:
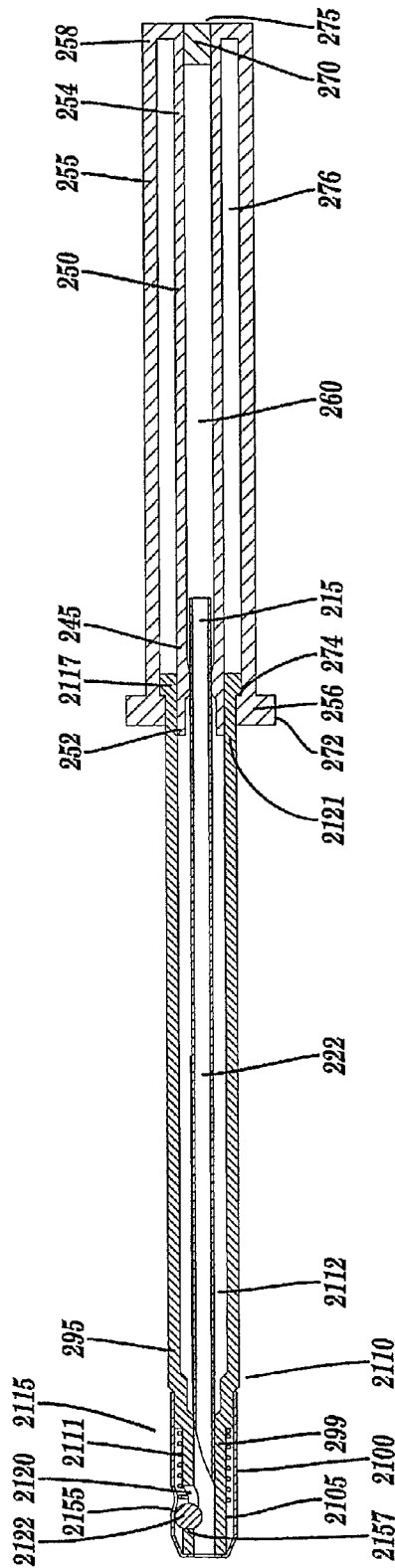
FIG. 10 is an orthogonal cross-sectional view through a catheter introducer assembly with the needle shield in a deployed position.

The position of ball 122 in opening 120 and partially occluding lumen 93 is shown in FIGS. 5 & 7. When ball 122 has moved to the point where it partially occludes lumen 93 as described, area of enlarged cross section 14 abuts rear opening 140 of cap 100, and further pulling of needle 10 causes shield assembly 90 to come out of catheter hub 52 due to the fact that ball 122 is no longer in groove 75. The force of groove 75 against ball 122 due to the pulling of the needle in a proximal direction may also urge ball 122 radially into lumen 93.

Movement of the shield assembly in the distal direction (such that shield assembly 90 slides off distal end 20 of the needle) is prevented by the interaction of area of enlarged cross section 14 on needle 10 and rear opening 140 of second housing 100. Movement of the shield assembly in the proximal direction (to expose needle tip 25) is prevented by distal end 20 of needle 10 abutting ball 122.

The distance from enlarged cross section 14 to tip 25 is set so that when tip 25 is aligned with ball 122, there is sufficient space for the ball to move beneath second housing 100 in opening 120. The angle formed by upper surface 136 tangential to ball 122 is as described above with reference to FIG. 3. Distal end 97 of first housing 95 and cap 100 are dimensioned to overhang so that tip 25 can never emerge from distal end 97 of shield 90. It is possible to employ multiple balls sitting in multiple openings the same as openings 120 and 150. If this is done, the overhang on distal end 97 and cap 100 can be reduced, making shield assembly 90 more compact.

After deployment, but before needle 10 moves distally, part of ball 122 lies in lumen 93 and part of it is urged against distal wall 157 of opening 120 by spring 110. The top of ball 122 lies beneath distal end 135 of second housing 100. In an alternative embodiment, spring 110, having expanded, closes off the top of opening 120. Ball 122 is thus radially and axially constrained in opening 120. If needle 10 moves distally, it will abut ball 122, which will be forced against distal wall 157 of second housing 100 and surface 136. Further distal movement of needle 10 and hence emergence of needle tip 25 from the shield assembly will be prevented.

Lumen 93 is sized such that needle 10 fits relatively snugly inside it. Thus, when needle 10 is moved distally (i.e. shield 90 is moved proximally) and ball 122 abuts needle tip 25, needle 10 will not move away from ball 122. Lumen 93 thus provides support opposite ball 122 to prevent needle 10 from wiggling, and to prevent tip 25 from moving such that it pierces first housing 95. The snugness of the fit between lumen 93 and needle 10 also facilitates the threading of shield 90 onto needle 10 (i.e. the distal end of shield 90 is threaded onto the proximal end of the needle). The snug fit means that the shield is guided so that proximal end 15 of needle 10 enters opening 140 in proximal end 130 of cap 100. This is important because opening 140 is typically only 0.001 inch larger than the diameter of needle 10.

In an alternative embodiment, ball 122 fully enters lumen 93. Ball 122 has a diameter slightly larger than that of lumen 93. Ball 122 is then axially constrained by lumen 93 and needle 10. In this case, lumen 93 is also dimensioned to provide support for needle 10 opposite ball 122, thus preventing wiggle of the needle and preventing tip 25 from piercing first housing 95.

In order to move out of groove 75 ball 122 moves a distance at least equal to the amount by which it protrudes from opening 150 plus the wall thickness of cap 100 (approx. 0.003" to 0.005"). When the shield is deployed ball 122 extends into lumen 93 by an amount approximately equal to that distance. This leaves part of lumen 93 occluded. If a small gauge needle is used, a larger ball is needed in order to occlude lumen 93 sufficiently to prevent needle tip 25 from poking through the un-occluded part of lumen 93. If a large gauge needle is used, the ball can be smaller (i.e if the needle has a large diameter, the ball can be smaller).

The above description includes operation of needle shield 90 with catheter assembly 50, providing, in addition to a needle shielding function, a mechanism for locking shield 90 to catheter assembly 50 and unlocking it. This provides the added benefit of ensuring that shield 90 can never be removed from catheter hub 52 until needle tip 25 is shielded. In cases where a catheter lock is not needed, cap 100 can be closed (i.e. lack opening 120) and slightly enlarged to accommodate the entire diameter of ball 122.

The following is a description of a second type of catheter introducer assembly embodying the invention. In this second type of catheter introducer, when the needle is shielded, a tube covers the entire length of the needle and restrains the needle shield from further distal movement. Reference is made to FIGS. 9-14.

The body is pierced by needle 210, which has an outer surface 212, a proximal end 215, a distal end 220 and a lumen 222. Distal end 220 has a sharp point 225. Distal end is beveled, with two bevels—surfaces 230 and 240 forming a slope extending from the sharp point 225 in a proximal direction. More or less than two bevels may be used. Proximal end 215 is secured to needle hub 245.

Needle hub 245 has a tube 250 extending backwards from where it is secured to proximal end 215 of needle 210. Needle hub tube 250 has a proximal end 254 and a distal end 252 (to which needle 210 is secured). Needle hub tube 250 has lumen 260 which is coaxial with lumen 220 of needle 210 so that fluid can flow along lumen 222 and into lumen 260. Needle hub tube 250 is integral and coaxial with another tube 255 which forms a handle and has proximal end 258 and distal end 256. Tubes 250 and 255 are joined at the back 275 (proximal end) of the assembly. That is to say proximal end 254 of needle tube 250 and proximal end 258 of handle tube 255 are joined at back 275. Needle hub 250 is open at the back (has hole 270), which is fitted with a vent plug to permit air but not liquid to escape as fluid enters lumen 222 and flows into lumen 260. Both tubes 250 and 255 are transparent (or at least have a transparent part) so that the flow of fluid can be seen by the user. Tube 255 has an exterior circumferential flange 272 located at distal end 256, approximately in line with the area where proximal end 215 of needle 210 is secured to needle hub 245. Tube 255 also has an interior circumferential flange 274 substantially in line with exterior flange 272. The combination of needle hub tube 250 and handle tube 255 can be regarded as two concentric cylinders. Between tubes 250 and 255 is an annular space 276 which extends from distal end 256 to back 275.

Catheter assembly 280 has a catheter adapter or hub 282 having proximal end 285, distal end 288 and lumen 290 extending between the proximal and distal ends. Catheter tube 286 extends distally out of distal end 288. Needle 210 lies within lumen 290 of catheter assembly 280 prior to insertion into the body. Once needle 210 has been inserted into the patient, together with catheter tube 286 needle 210 is withdrawn by pulling it in a proximal direction. Catheter hub 282 has an inner surface 292 and an outer surface 291. Inner surface 292 is provided with a circumferential groove 293, the purpose of which has been explained above and will be explained in due course. A single depression, indentation, circumferential ridge or raised portion will serve the same purpose as the circumferential groove.

Needle shield assembly 2110 has a proximal end 2120, a distal end 2115 and a lumen 2112 extending from the proximal to the distal end. Lumen 2112 is dimensioned at distal end 2115 so that shield assembly 2110 can slide axially and rotate on needle 210. Shield assembly 2110 includes two parts—first housing 295 and cap 2100. Cap 2100 is at distal end 2115 and fits inside catheter hub 282. Shield 2110 is concentric with tubes 250 and 255. First housing 295 of shield 2110 lies at least partially in annular space 276 when the shield is in its non-deployed position. First housing 295 can slide back and forth in an axial direction in annular space 276. First housing 295 is also at least partially transparent to permit the user to see fluid flow. Proximal end 2120 of shield 2110 is provided with circumferential flange 2117. When shield 2110 moves in a distal direction axially along annular space 276, flange 2117 will eventually abut interior flange 274 of handle tube 255 and will be prevented from further distal movement. In the deployed position, proximal end 2121 abuts interior flange 274 at distal end 256 of handle tube 255.

First housing 295 has a distal end 297 with stepped area 2105—an area of reduced diameter which allows coil spring 2111 to be placed on first housing 295 and cap 2100 to be placed over it. Stepped area 2105 can be formed separately from first housing 295 and attached to it. Spring 2111 is a compression spring, which exerts a force axially in the proximal and distal directions. Towards distal end 297 of first housing 295, but still in the stepped area 2105, first housing is provided with an opening 2120, dimensioned to accommodate ball 2122.

Cap 2100 is a metal stamping having a proximal end 2130 and a distal end 2135. When first housing 295 and cap 2100 are assembled, second housing 2100 covers distal end 297 of the first housing and spring 2111. Cap 2100 is provided with opening 2150 which is dimensioned such that part of ball 2122 can protrude through it and into groove 293. Cap 2100 is dimensioned to fit in catheter hub 282. The part of first housing 295 immediately adjacent stepped area 2104 also fits in catheter hub 282.

Figure 11:
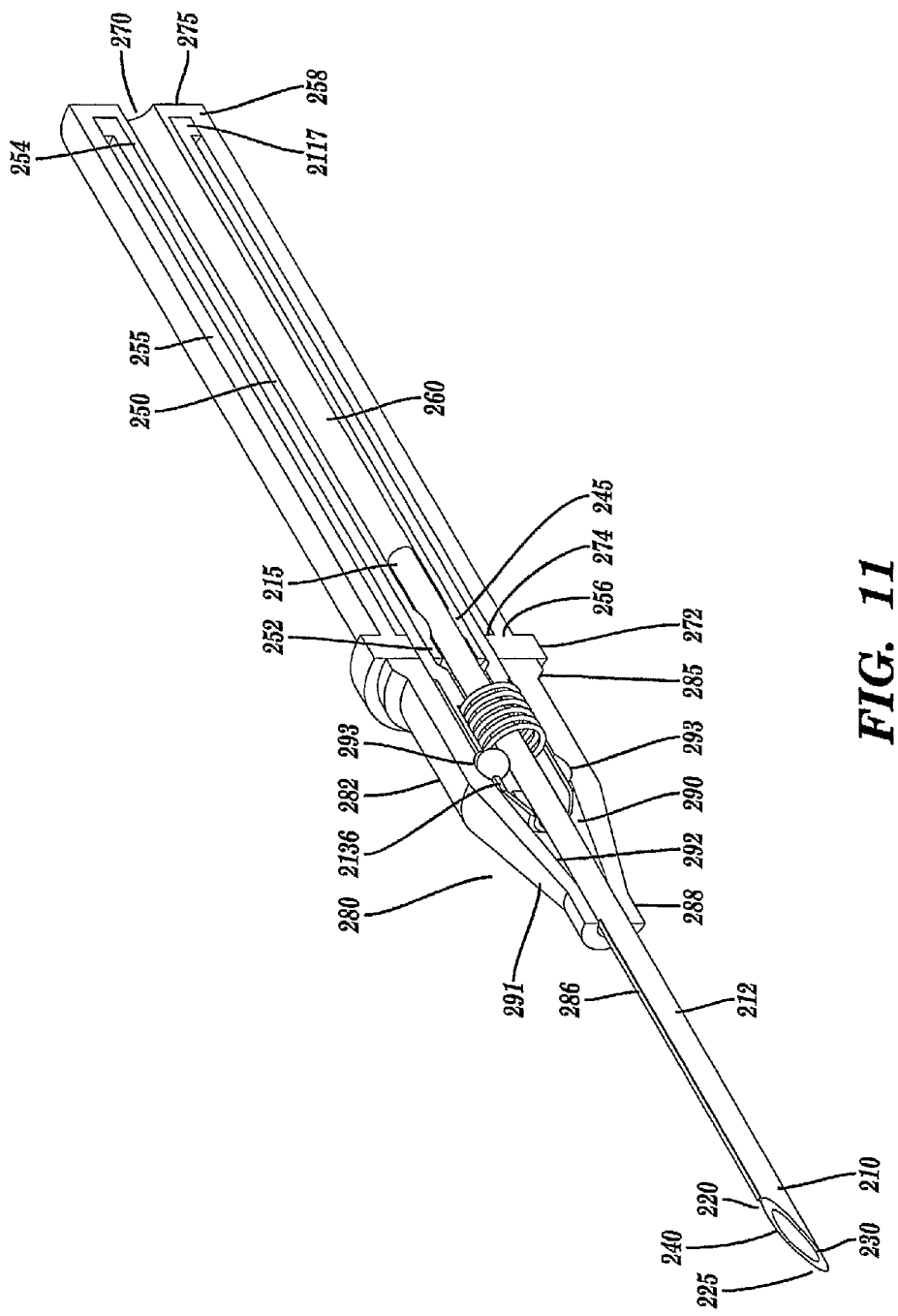
FIG. 11 is an isometric cross-sectional view through a catheter introducer assembly with the needle shield in a non-deployed position.
Figure 12:
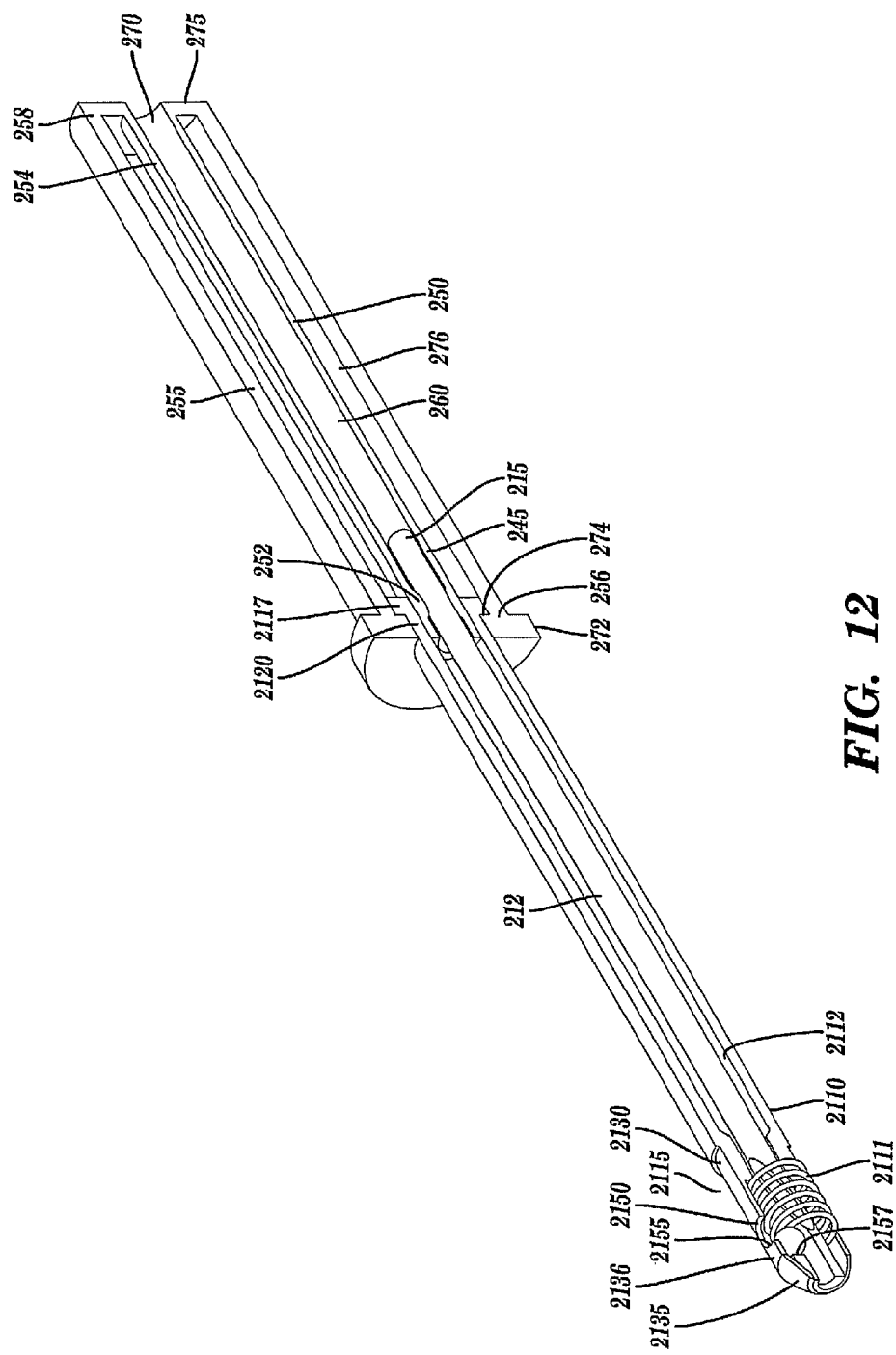
FIG. 12 is an isometric cross-sectional view through a catheter introducer assembly with the needle shield in a deployed position.
Figure 13:
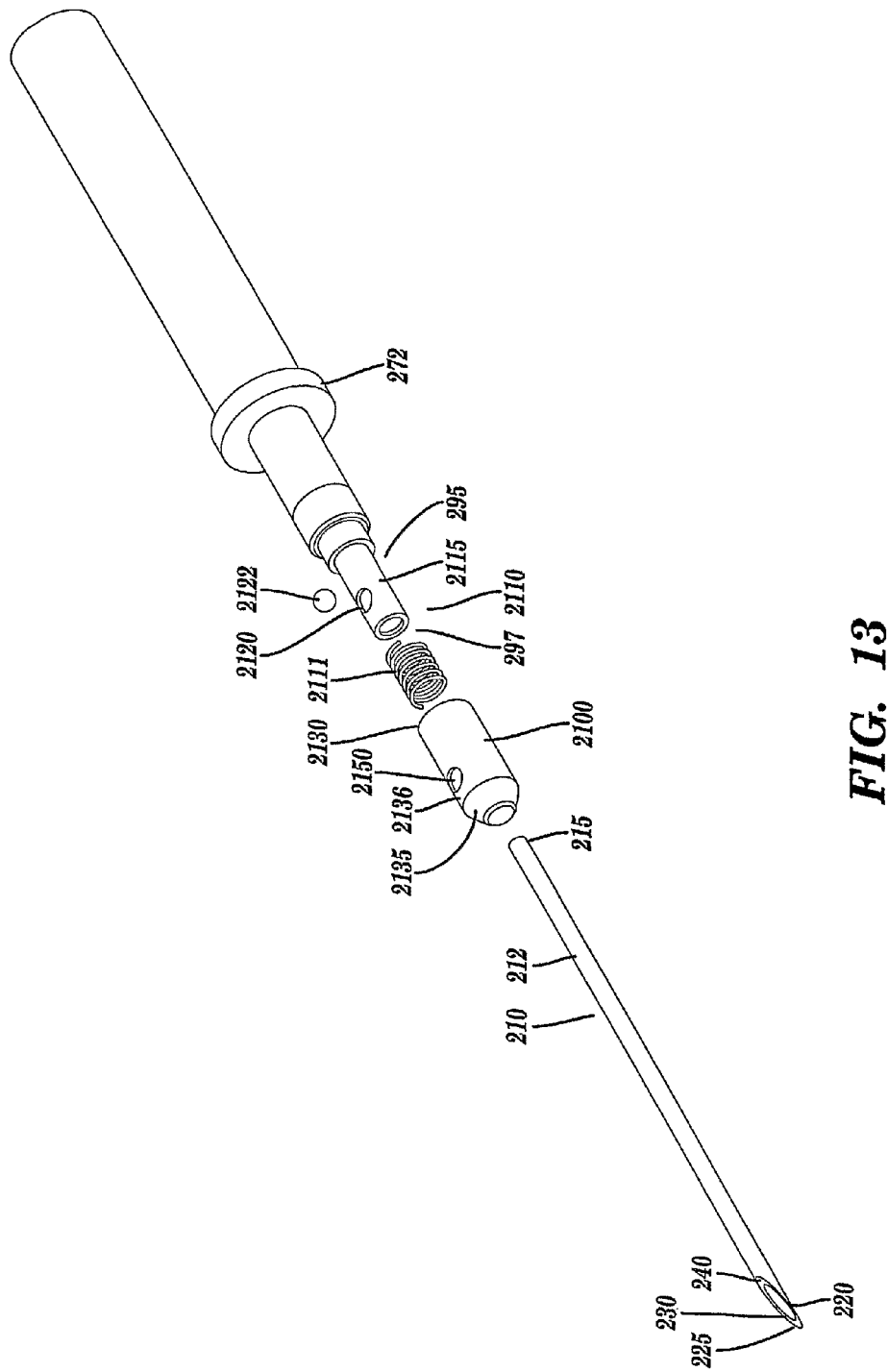
FIG. 13 is an exploded view of the components of the needle shielding device and the needle hub.

When needle shield assembly 2110 is attached to catheter hub 282 (i.e. cap 2100 and part of first housing 295 are in catheter hub 282), prior to deployment, part of ball 2122 protrudes through opening 2150 and lies in groove 293. This locks needle shield assembly 2110 to catheter hub 282, while allowing catheter hub 282 to rotate relative to needle shield assembly 2110, depending on the extent of groove 293 (i.e. whether it is circumferential or permits only limited movement because it does not extend around the entire inner circumference of the catheter hub). Part of ball 2122 also lies in lumen 2112 of first shield assembly 2110 and abuts outer surface 212 of needle 210 (i.e. ball 2122 touches outer wall 212 of needle 210). Needle 210 and shield assembly 2110 can slide and rotate relative to each other with very low friction. Ball 2122 is radially constrained by groove 293 and needle 210. Needle shield assembly 2110 is thus locked into catheter hub 282. Spring 2111 exerts a force on ball 2122 axially, in the distal direction. Moreover, the presence of needle 10 abutting ball 2122 radially constrains ball 2122 and prevents it from moving out of groove 293. This is shown in FIG. 11.

Once catheter tube 286 has been placed in the patient, needle 210 is pulled in a proximal direction (that is to say, as needle shield assembly 2110 moves towards tip 225 of needle 210 or needle hub 245 is pulled proximally). If bevels 230 and 240 are facing ball 2122, then, when first bevel 240 comes into alignment with ball 2122, ball 2122 is less radially constrained by needle and, urged by spring 2111, it begins to move in opening 2120, distally and radially. Ball 2122 thus moves out of opening 2150 in cap 2100 and groove 293 in catheter hub 282 and radially inwards further into lumen 2112 of shield assembly 2110, pivoting about edge 2155, (a wall of opening 2150 in cap 2100) and sliding distally along the length of opening 2120. When second bevel 230 is aligned with ball 2122, needle 210 no longer constrains it radially and it moves completely out of groove 293. When ball 2122 is positioned such that edge 2155 is above it, ball 2122 will have traveled radially into lumen 1212 as far as it can, constrained by the dimensions of opening 2120 and partially occluding lumen 2112.

If bevels 230 and 240 are not facing ball 2122 or are partially facing ball 2122, the device operates in a similar manner as described above. Spring 2111 urges ball 2122 along opening 2120 so that ball 2122 moves out of groove 293 and pivots about edge 2155. Ball 2122 is constrained from entering lumen 293 by the dimensions and geometry of opening 2120. Ball 2122 thus partially occludes lumen 2112.

After ball 2122 has moved to the point where it partially occludes lumen 2112 as described, flange 2117 of shield assembly 2110 abuts interior flange 274 of tube 255, and further pulling of needle 210 causes shield assembly 2110 to come out of catheter hub 282 due to the fact that ball 2122 is no longer in groove 293. The force of groove 293 against ball 2122 due to the pulling of the needle in a proximal direction may also urge ball 2122 radially into lumen 2112.

Movement of the shield assembly in the distal direction (such that shield assembly 2110 eventually slides off distal end 220 of the needle) is prevented by the interaction of flanges 274 and 2117. Movement of the shield assembly in the proximal direction (to expose needle tip 225) is prevented by distal end 220 of needle 210 abutting ball 2122 which abuts wall 2157 of first housing 295 and upper inner wall 2136 of second housing or cap 2100.

The distance from flange 2117 to needle tip 225 is set so that when tip 225 is aligned with ball 2122, there is sufficient space for the ball to move beneath cap 2100 in opening 2120. The considerations for angles α and β (i.e. the tangent formed between ball 2122 and surface 2136 and the smallest bevel angle) are as set forth above in relation to FIG. 3.

After deployment, but before needle 210 moves distally, part of ball 2122 lies in lumen 2112 and part of it is urged against distal wall 2157 of opening 2120 by spring 2111. The top of ball 2122 lies beneath upper surface 2136 of distal end 2135 of cap 2100. Distal end 299 of first housing 295 and cap 2100 are likewise dimensioned to overhang so that tip 225 can never emerge from distal end 2115. Multiple balls can likewise be used. The foregoing design also provides a catheter locking feature as previously described.

Once the shield has been deployed, but before needle 210 moves distally, part of ball 2122 lies in lumen 2112 and part of it is urged against wall 2157 of opening 2120 by spring 2111. The top of ball 2122 lies beneath upper surface 2136 of distal end 2135 of cap 2100. Opening 2120 may be closed off by spring 2111. Ball 2122 is radially and axially constrained in opening 2120. If needle 210 moves distally, it will abut ball 2122, which will be forced against distal wall 2157 of first housing 295 and wall 2136 of cap 2100. Needle 210 thus cannot emerge distally from the shield.

Lumen 2112 provides anti-wiggle support for needle 210 as described above in relation to an earlier embodiment. Similar considerations as described above apply to movement of the ball and the dimensions of the ball relative to the needle gauge size. That is to say, larger balls are used for smaller gauge sizes and vice versa.

Figure 14:
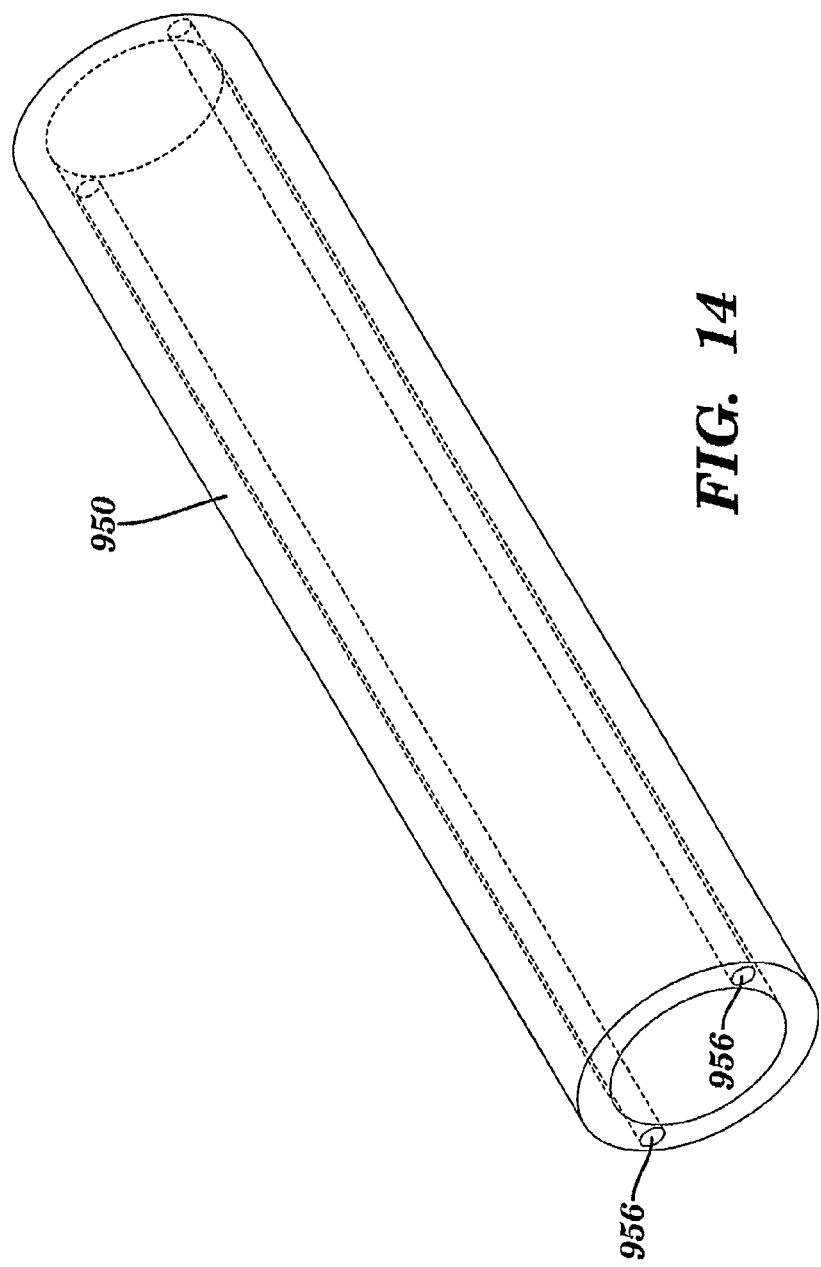
FIG. 14 is an isometric view of an extruded polymeric tube used in one embodiment of the invention.
Figure 15:
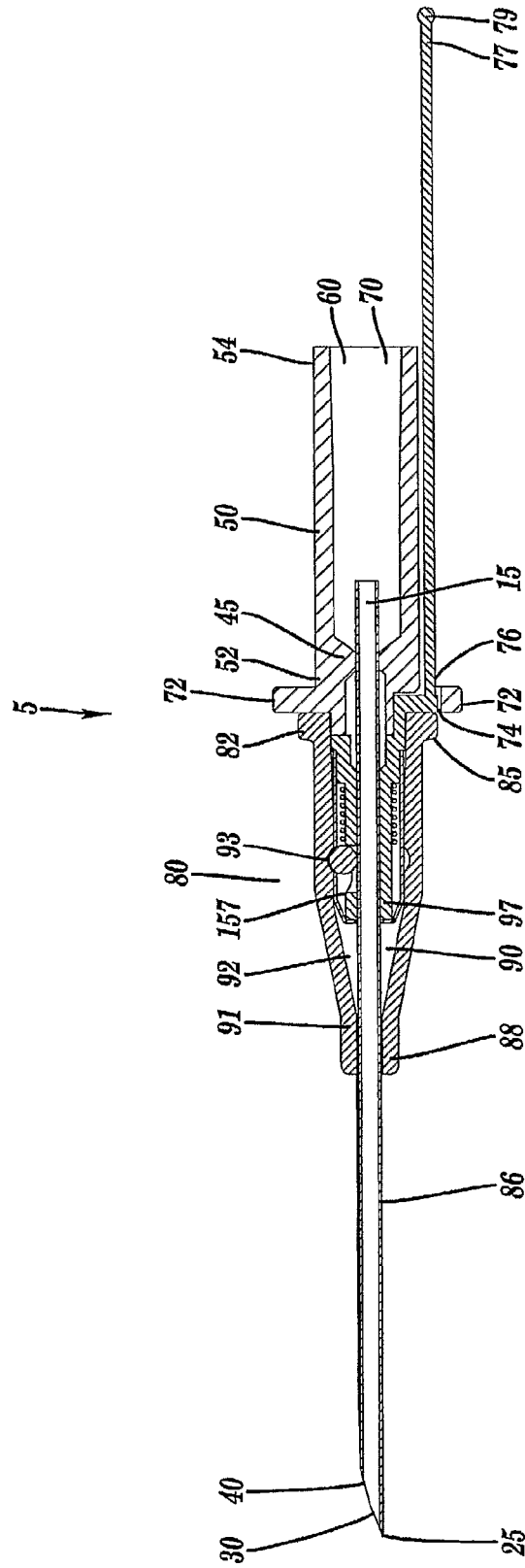
FIG. 15 is an orthogonal cross-sectional view through a catheter introducer assembly with the needle shield in a non-deployed position.
Figure 16:
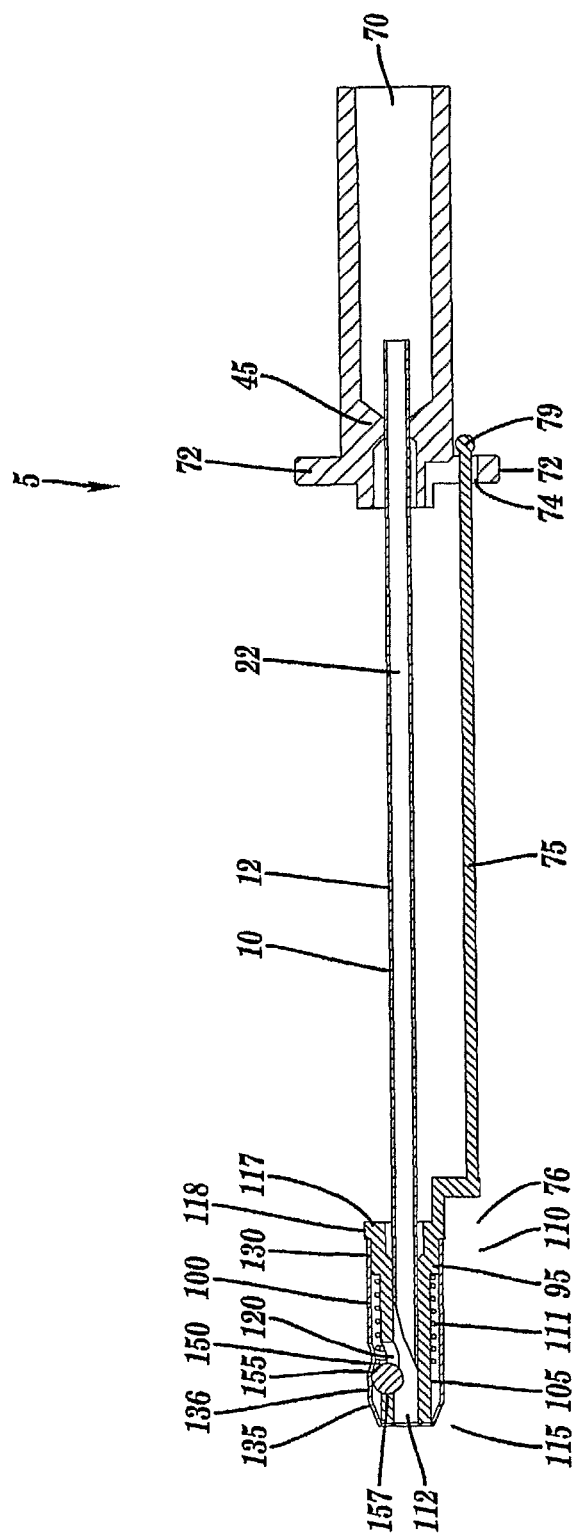
FIG. 16 is an orthogonal cross-sectional view through a catheter introducer assembly with the needle shield in a deployed position.
Figure 17:
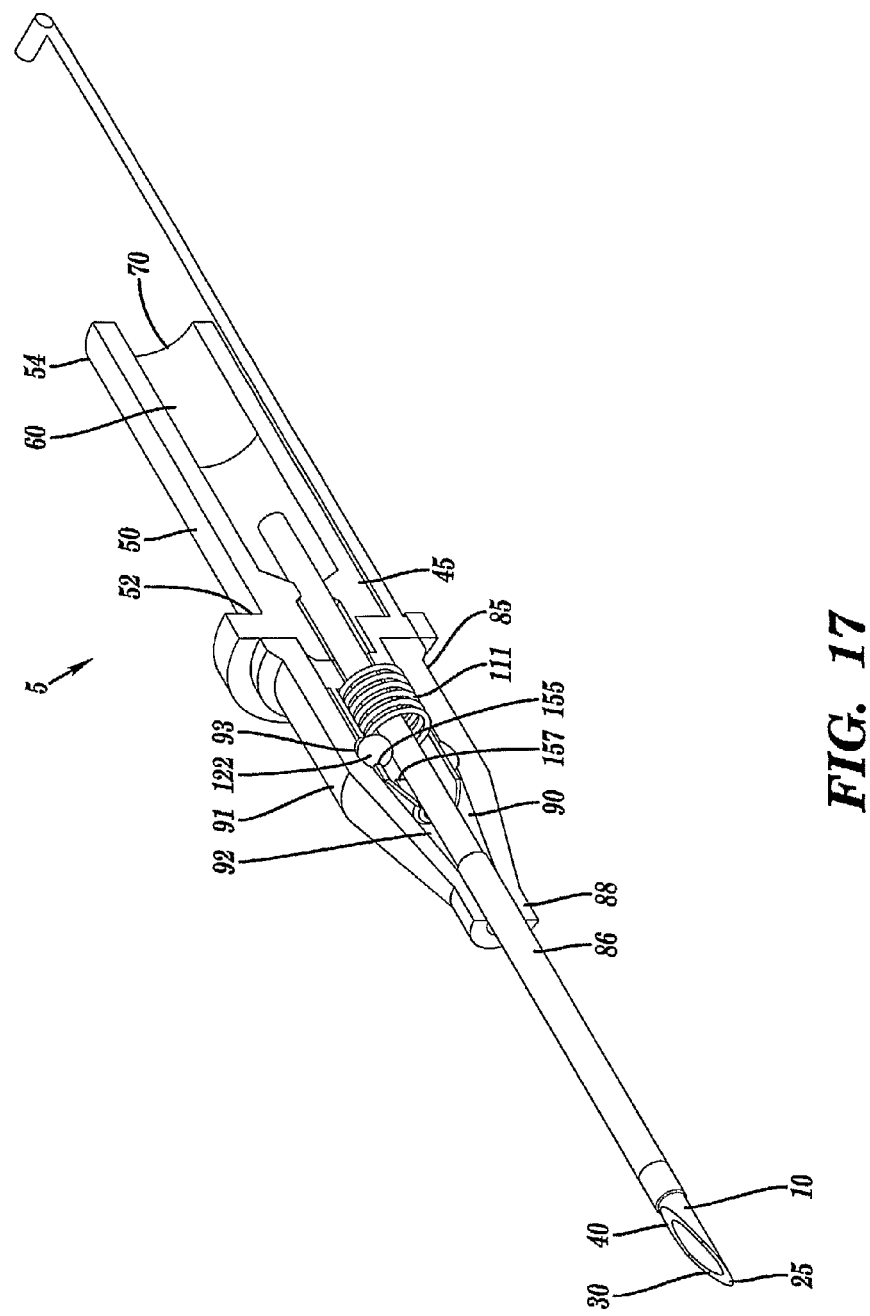
FIG. 17 is an isometric cross-sectional view through a catheter introducer assembly with the needle shield in a non-deployed position.
Figure 18:
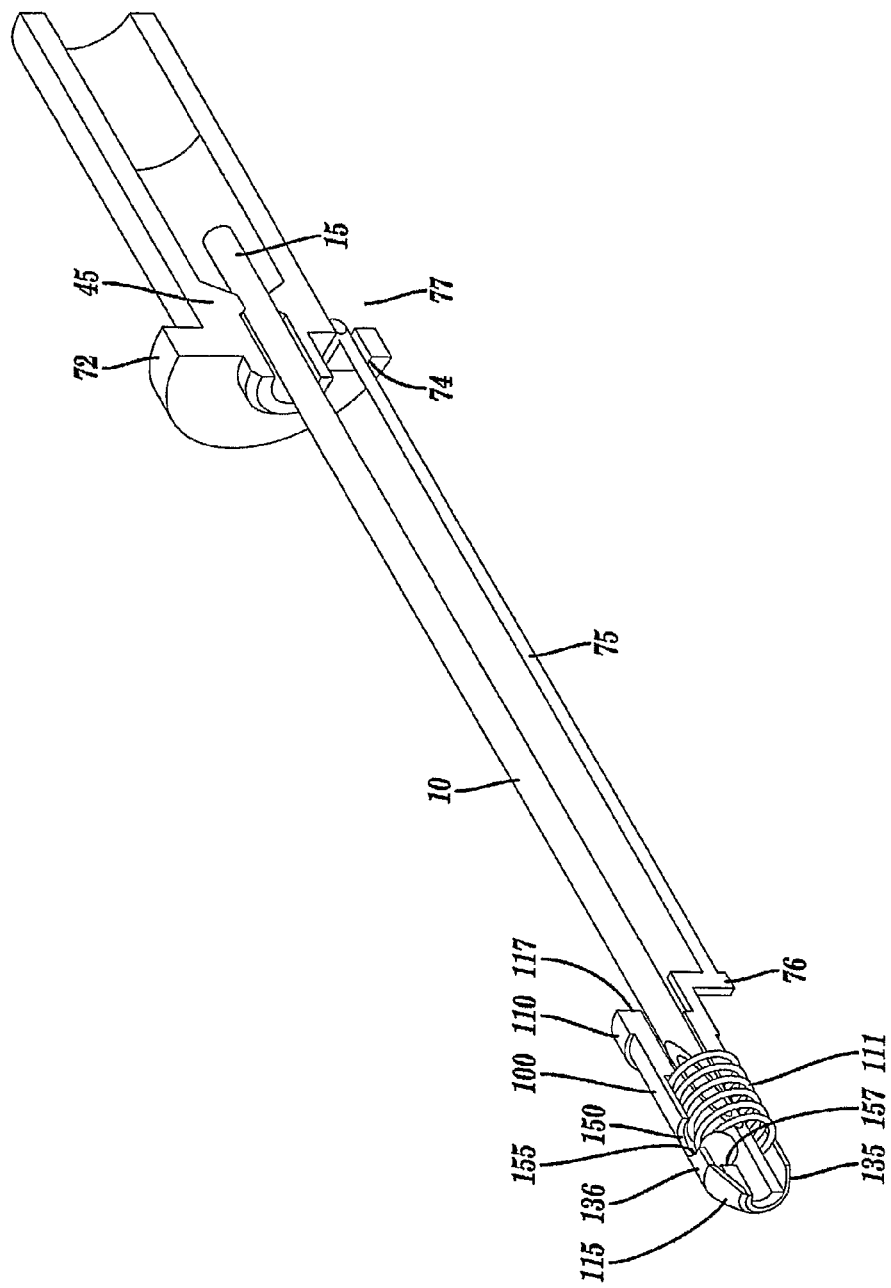
FIG. 18 is an isometric cross-sectional view through a catheter introducer assembly with the needle shield in a deployed position.
Figure 19:
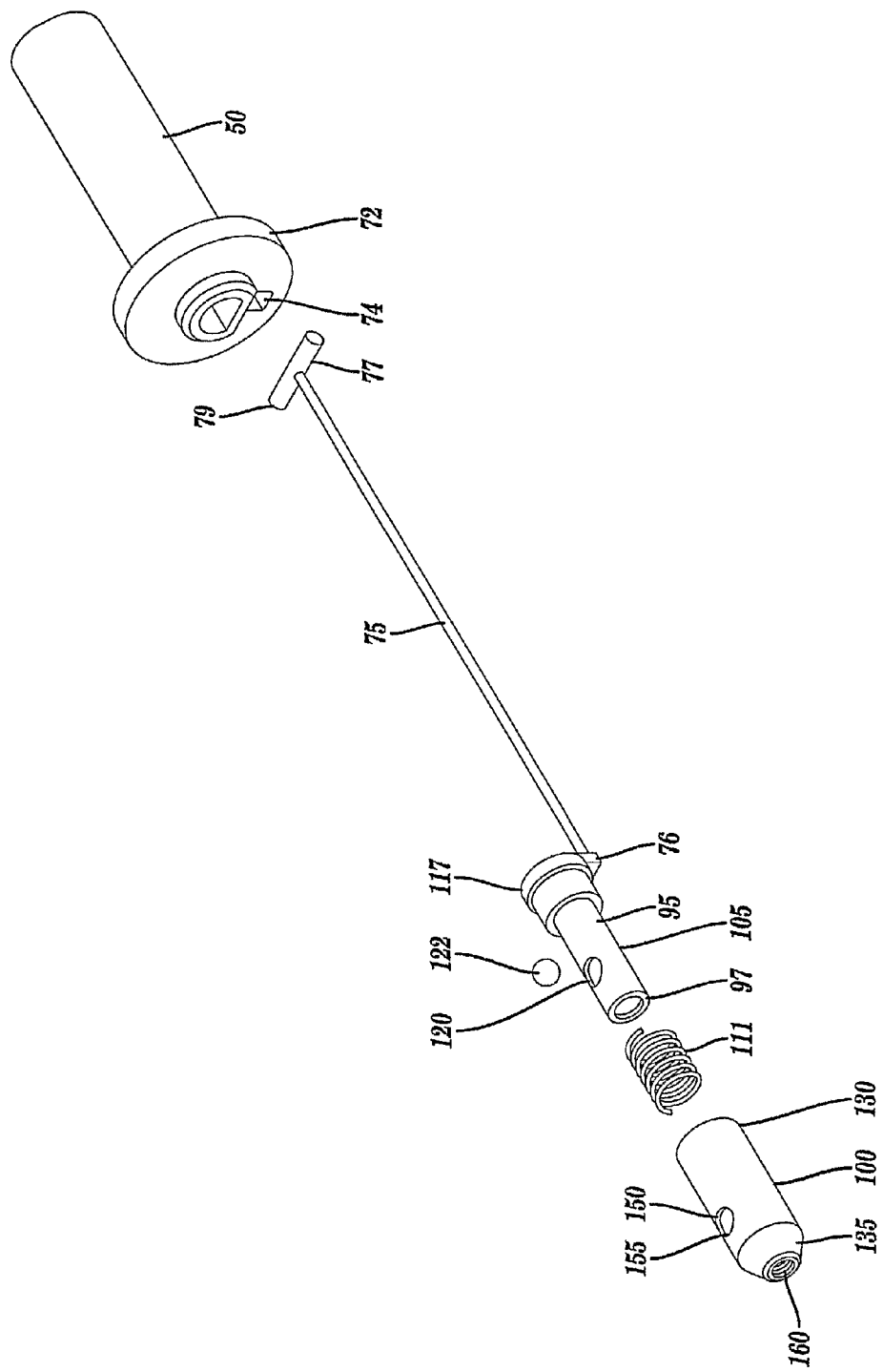
FIG. 19 is an exploded view of the components of the needle shielding device and the needle hub.
Figure 22:
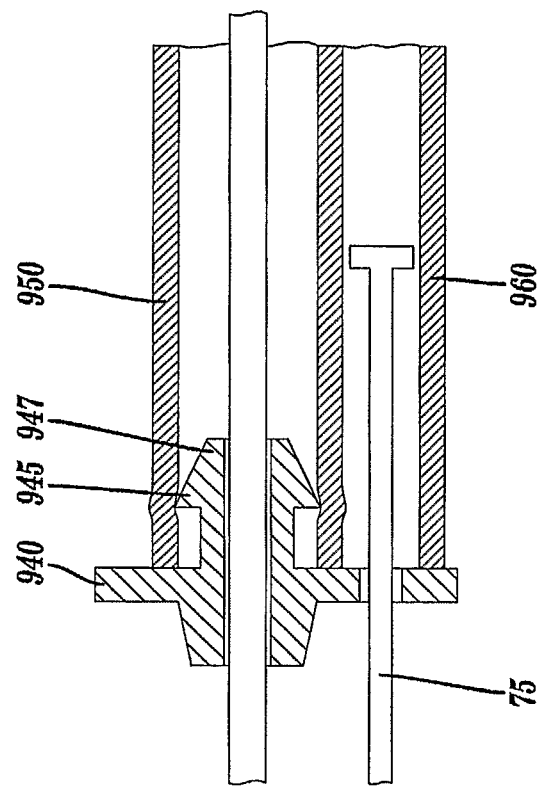
FIG. 22 is an orthogonal cross-sectional view of the housing of the embodiment of FIG. 20.
Figure 21:
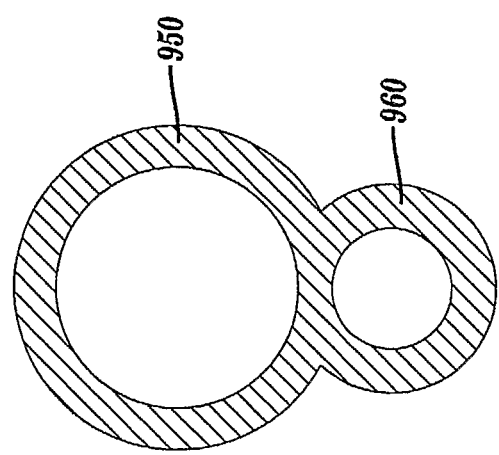
FIG. 21 is a cross-sectional through the housing of the embodiment of FIG. 20.
Figure 23:
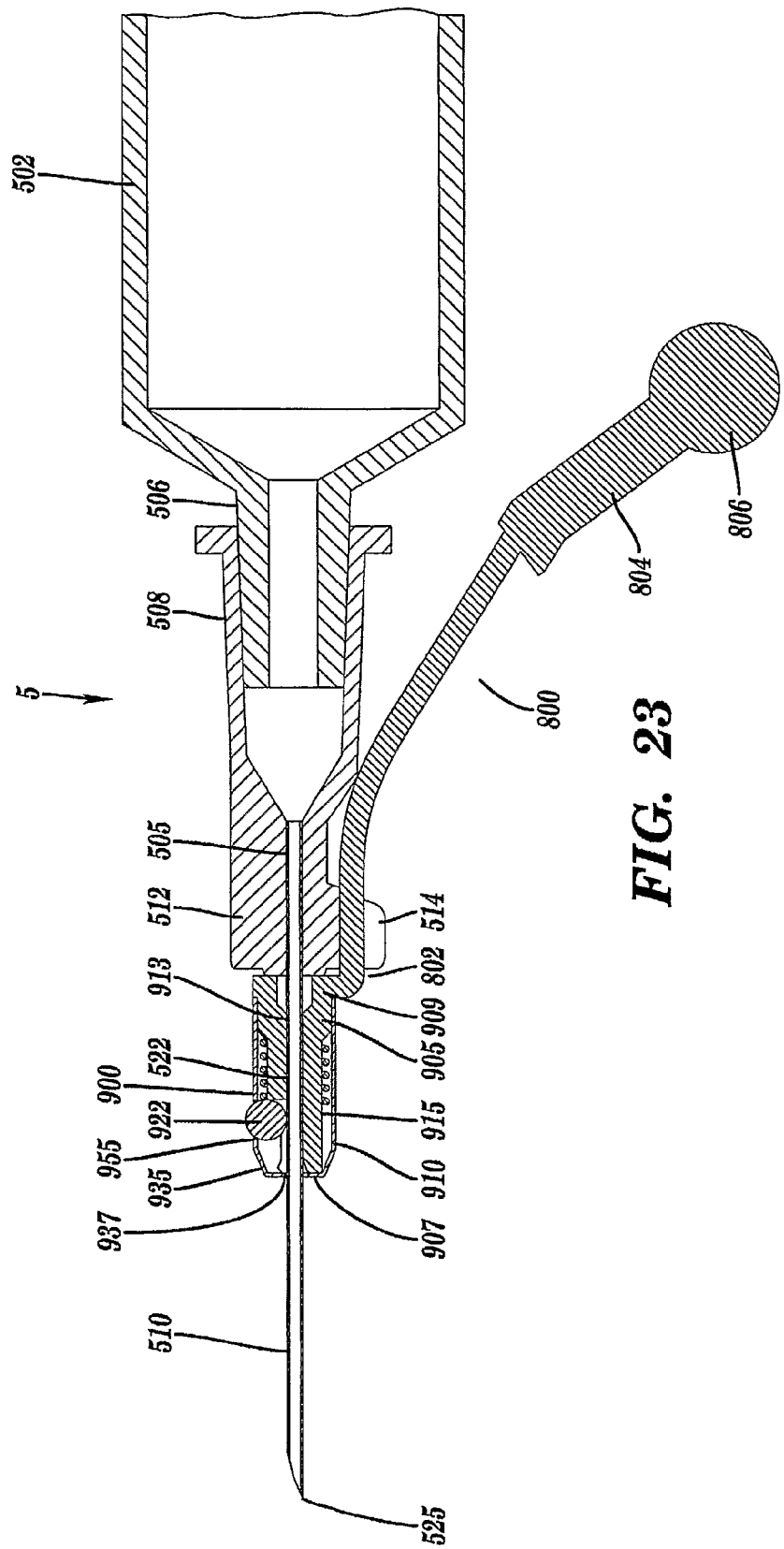
FIG. 23 is an orthogonal cross-sectional view through a syringe needle shielding apparatus with the needle shield in a non-deployed position.
Figure 24:
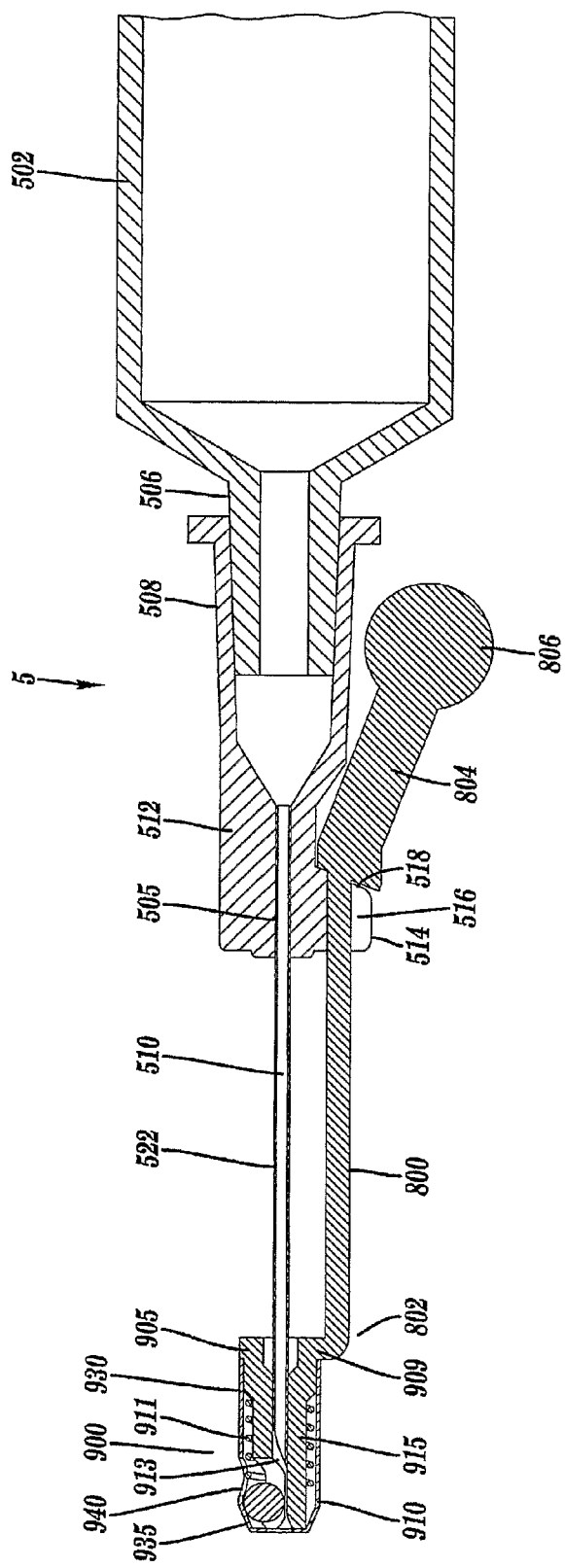
FIG. 24 is an orthogonal cross-sectional view through a syringe needle shielding apparatus with the needle shield in a deployed position.
Figure 25:
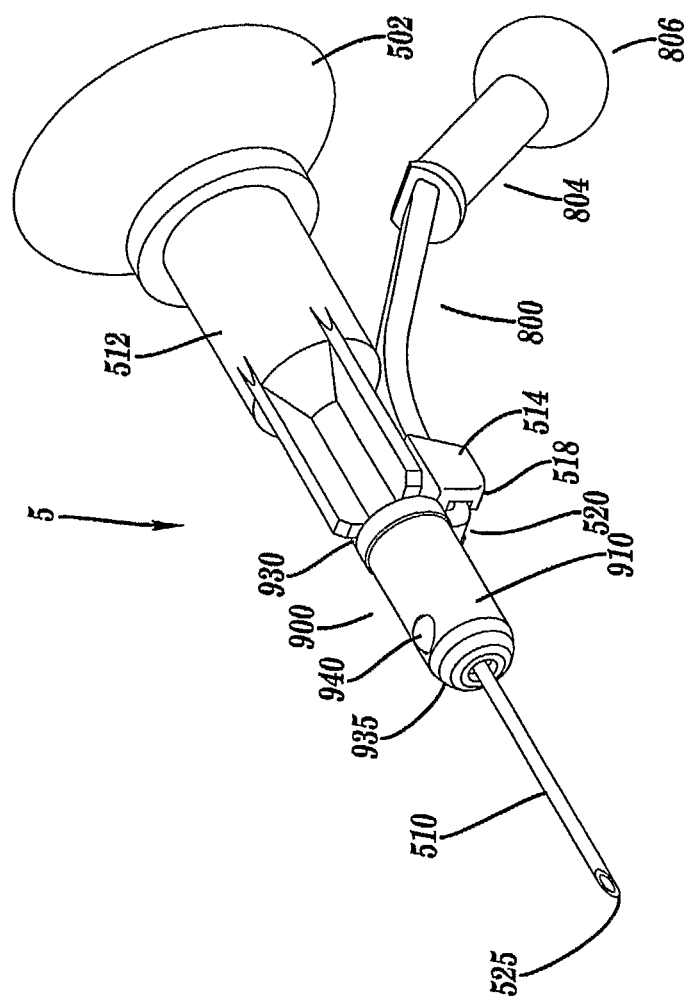
FIG. 25 is an isometric view of a syringe needle shielding apparatus with the needle shield in a non-deployed position.
Figure 26:
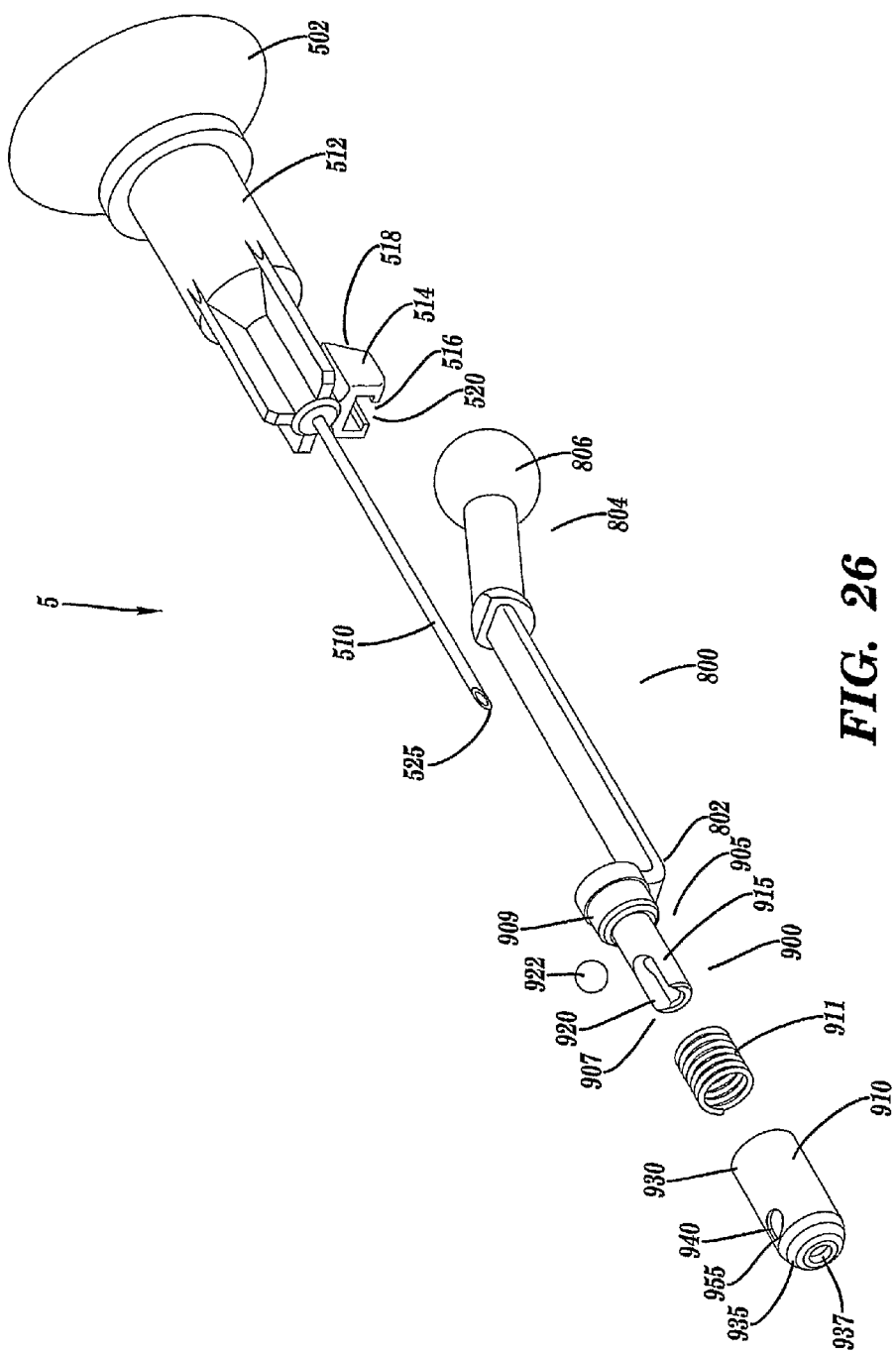
FIG. 26 is an exploded view of the components of the syringe needle shielding apparatus.

First housing 295 and the tube part of shield 2110 can be made out of an extruded polymeric tube 950 as shown in FIG. 14 (see also FIGS. 20-22). Polymeric tube 950 is relatively thin and flexible. This, and the fact that it is extruded, makes it extremely light and simple to manufacture and the amount of materials needed to manufacture it is reduced relative to rigid molded members. In order to provide stiffness and strength, the polymeric tube may be reinforced with coextruded metal wires 956. Wires 956 are shown as longitudinal wires running along the length of tube 955. Alternatives to longitudinal wires are a coextruded woven fabric, mesh, lattice or spiral.

The following is a description of a catheter introducer assembly embodying the invention, in which distal movement of the needle shield is restrained by a tether secured to the needle hub. Reference is made to FIGS. 15-19. Needle hub 45 has a tube 50 extending backwards from where it is secured to proximal end 15 of needle 10. Needle hub tube 50 has a proximal end 54 and a distal end 52 (to which needle 10 is secured). Needle hub tube 50 has lumen 60 which is coaxial with lumen 22 of needle 10 so that fluid can flow along lumen 22 and into lumen 60. Needle hub tube 50 forms a handle by which the user can grasp catheter assembly 5 in order to insert needle 10 into a patient.

Needle hub 50 is open at the back (has hole 70), which may be fitted with a vent plug to permit air but not liquid to escape as fluid enters lumen 22 and flows into lumen 60. Tube 50 is transparent (or at least has a transparent part) so that the flow of fluid can be seen by the user. Tube 50 has an exterior circumferential flange 72 located at distal end 52, approximately in line with the area where proximal end 15 of needle 10 is secured to needle hub 45.

Circumferential flange 72 is provided with a small opening 74, through which is threaded tether 75. Tether 75 has a proximal end 77 and a distal end 76. Proximal end is T-shaped. Arm 79 of the T prevents tether 75 from escaping through opening 74 when tether 75 moves distally. Distal end 76 is secured to needle shield assembly 110 (described below). Tether 75 thus prevents needle shield assembly from moving off tip 25 of needle 10 in the distal direction. Tether 75 can be made of nylon and closely resembles a label holder used in the retail industry to secure labels to items of clothing. Tether 75 may be integrally molded with first housing 95 but does not have to be.

Catheter assembly 80 has a catheter hub 82 having proximal end 85, distal end 88 and lumen 90 extending between the proximal and distal ends. Catheter tube 86 extends distally out of distal end 88. Needle 10 lies within lumen 90 of catheter assembly 80 prior to insertion into the body. Once needle 10 has been inserted into the patient, together with catheter tube 86, needle 10 is withdrawn by pulling it in a proximal direction. Catheter hub 82 has an inner surface 92 and an outer surface 91. Inner surface 92 is provided with a circumferential groove 93, the purpose of which will be explained in due course. A single depression, indentation, circumferential ridge or raised portion will serve the same purpose as the circumferential groove.

Needle shield assembly 110 has a proximal end 118, a distal end 115 and a lumen 112 extending from the proximal to the distal end. Lumen 112 is dimensioned so that shield assembly 110 can slide axially and rotate on needle 10. Shield assembly 110 is contained in mating parts—first housing 95 and cap 100. Cap 100 is at distal end 115 and fits inside catheter assembly 80.

First housing 95 has a distal end 97 with stepped area 105—an area of reduced diameter which allows coil spring 111 to be placed on first housing 95 and cap 100 to be placed over it. Spring 111 is a compression spring, which exerts a force axially in the proximal and distal directions. Towards distal end 97 of first housing 95, but still in the stepped area 105, first housing is provided with an opening 120, dimensioned to accommodate ball 122.

Cap 100 is a metal stamping having a proximal end 130 and a distal end 135. Cap 100 covers distal end 97 of the first housing and spring 111. Cap 100 is provided with opening 150 which is dimensioned such that part of ball 122 can protrude through it and into groove 93. Cap 100 is dimensioned to fit in catheter hub 82. The part of first housing 95 immediately adjacent stepped area 104 also fits in catheter hub 82.

When needle shield assembly 110 is attached to catheter hub 82 (i.e. cap 100 and part of first housing 95 are in catheter hub 82), prior to deployment, part of ball 122 protrudes through opening 150 and lies in groove 93. This locks needle shield assembly 110 to catheter hub 82, while allowing catheter hub 82 to rotate relative to needle shield assembly 110, depending on the extent of groove 93 (i.e. whether it is circumferential or permits only limited movement because it does not extend around the entire inner circumference of the catheter hub). Part of ball 122 also lies in lumen 112 of first shield assembly 110 and abuts outer surface 12 of needle 10 (i.e. ball 122 touches outer wall 12 of needle 10). Needle 10 and shield assembly 110 can slide and rotate relative to each other with very low friction. Ball 122 is radially constrained by groove 93 and needle 10. Spring 111 exerts a force on ball 122 axially, in the distal direction. Moreover, the presence of needle 10 abutting ball 122 radially constrains ball 122 and prevents it from moving out of groove 93.

Figure 6:
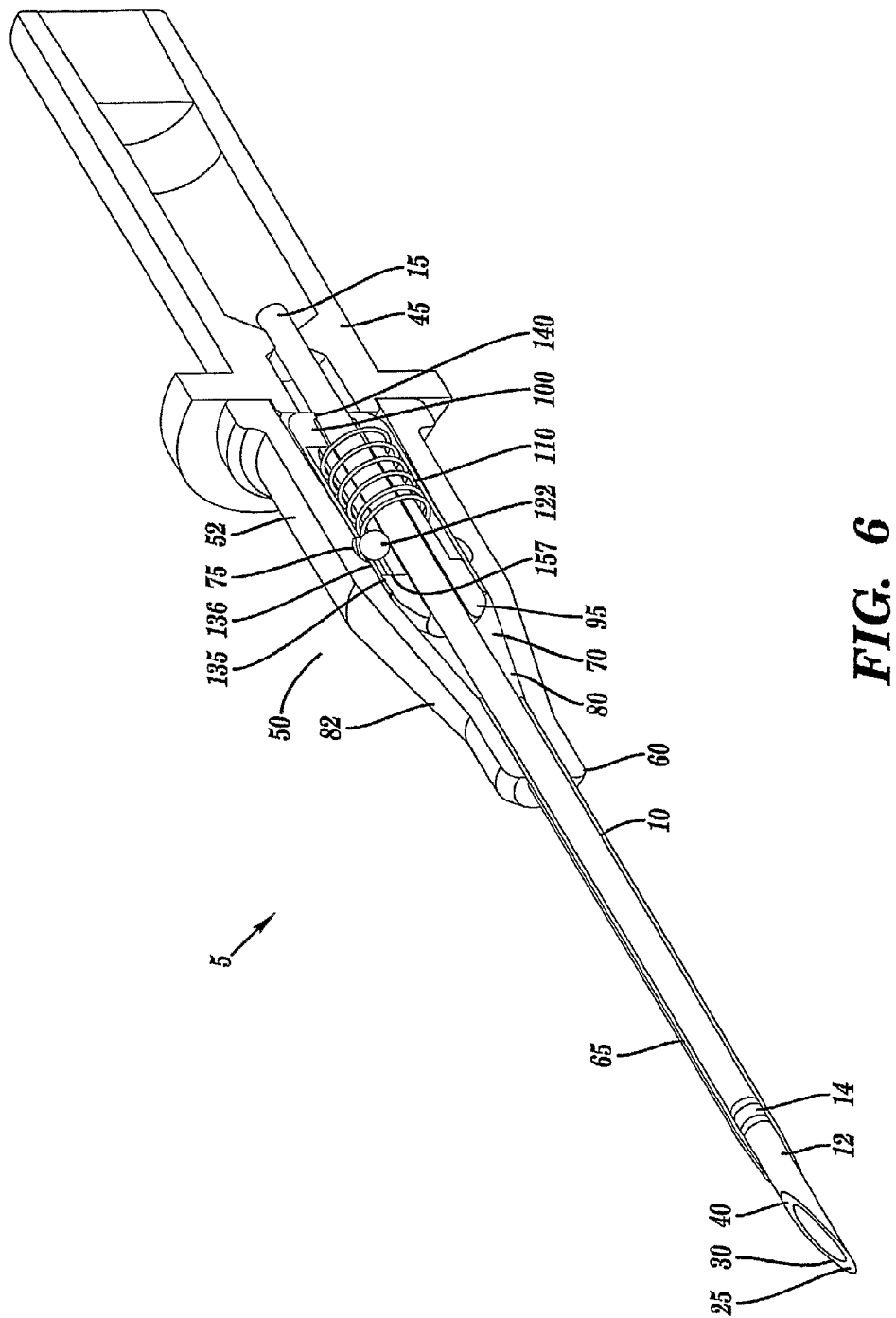
FIG. 6 is an isometric cross-sectional view through a catheter introducer assembly with the needle shield in a non-deployed position.

Once catheter tube 86 has been placed in the patient, needle 10 is pulled in a proximal direction (that is to say, as needle shield assembly 110 moves towards tip 25 of needle 10 or needle hub 45 is pulled proximally). If bevels 30 and 40 are facing ball 122, then, when first 20 bevel 40 comes into alignment with ball 122, ball 122 is less radially constrained by needle 10 and, urged by spring 111, it begins to move in opening 120, distally and radially. Ball 122 thus moves out of opening 150 in cap 100 and groove 93 in catheter hub 82 and radially inwards further into lumen 112 of shield assembly 110, pivoting about edge 155, (distal wall of opening 150 in cap 100) and sliding distally along the length of opening 120. When second bevel 30 is aligned with ball 122, needle 10 no longer constrains it radially and it moves completely out of groove 93. When ball 122 is positioned such that edge 155 is above it, ball 122 will have traveled radially into lumen 112 as far as it can, constrained by the dimensions of opening 120 and partially occluding lumen 112. This is shown in FIG. 6. The above operation is similar if bevels 30 and 40 are not facing ball 122, as described above in the context of another embodiment.

As needle hub 45 moves proximally, tether 75 plays out through opening 74, such that arm 79 moves distally. When ball 122 has moved to the point where it partially occludes lumen 112 as described, arm 79 of tether 75 abuts flange 72, and further pulling of needle 10 causes shield assembly 110 to come out of catheter hub 82 due to the fact that ball 122 is no longer in groove 93. The force of groove 93 against ball 122 due to the pulling of the needle in a proximal direction may also urge ball 122 radially into lumen 112.

Movement of the shield assembly in the distal direction (such that shield assembly 110 eventually slides off the distal end of the needle) is prevented by the interaction of arm 79 and flange 72. Movement of the shield assembly in the proximal direction (to expose needle tip 25) is prevented by distal end 20 of needle 10 abutting ball 122 which abuts wall 157 of opening 120.

The distance from tether arm 79 to needle tip 25 is set so that when tip 25 is aligned with ball 122, there is sufficient space for the ball to move beneath cap 100 in opening 120. The relationship between α (the tangential angle between ball 122 and upper surface 136 of distal end 135 of cap 100) and β (the smallest needle bevel angle) is described above, as are the considerations of the support provided by lumen 112 opposite ball 122 to prevent needle 10 from wiggling, and to prevent tip 25 from moving such that it pierces first housing 95. The relationship between ball and needle gauge size is also as described above.

As shown in FIG. 20, needle hub 45 in the embodiments shown in FIGS. 15-19 can be constructed out of a rigid plastic member 940, having barb 945 at its proximal end 947. Barb 945 mates with extruded polymeric tube 950 as shown in FIG. 22. Polymeric tube 950 is coextruded with lower tube 960, which forms a conduit along which tether 75 runs. Polymeric tubes 950 and 960 are relatively thin and 5 flexible. This, and the fact that they are extruded, makes the device extremely light and simple to manufacture and the amount of materials needed to manufacture it is reduced relative to rigid molded members. In order to provide stiffness and strength, polymeric tube may be reinforced with coextruded metal wires, woven fabric, wire mesh, wire lattice or spiral wires. This is shown in FIG. 14.

The following is a description of the application of the needle shield to a hypodermic syringe (a needle-based device without a catheter threaded onto it). Reference is made to FIGS. 23-26. Syringe and needle assembly 5 is made up of syringe body 502 with male luer adapter 506 with which female needle adapter 508 is mated. Needle adapter 508 has a hub 512 into which proximal end 505 of needle 510 is bonded. Needle 510 has a sharp distal end 525.

Needle shield assembly 900 is made up of two mating parts—first housing 905 and second housing or cap 910. First housing 905 has a proximal end 909 and a distal end 907. Extending between the proximal and distal ends is lumen 913, which is dimensioned so that first housing 905 can slide axially on needle 10. Extending from proximal end 909 towards distal end 907 is stepped area 915. This is an area of reduced diameter which allows coil spring 911 to be placed on first housing 905. Spring 911 is a compression spring, which exerts a force axially in the proximal and distal directions. Towards distal end 907 of first housing 905, but still in the stepped area 915, first housing is provided with an opening 920, dimensioned to accommodate ball 922.

Second housing or cap 910 has a proximal end 930 and a distal end 935. Proximal end 930 is provided with opening 937 which is dimensioned such that it is slightly larger than the diameter of needle 510. Thus, second housing 910 can slide axially along the needle from proximal end 505 towards distal end 525. When first and second housings 905 and 910 are assembled, second housing 910 covers most of first housing 905, except for the proximal end. Second housing thus covers spring 911. Second housing 910 is provided with opening 940 which is dimensioned such that part of ball 922 can protrude through it. This makes needle shield assembly 900 very compact. However, second housing 910 can me made slightly larger or provided with a blister to accommodate ball 922, so that ball 922 is completely covered.

When needle shield assembly is at needle hub 512, prior to deployment, part of ball 922 protrudes through opening 940. Part of ball 922 also lies in lumen 913 of first housing 905 and abuts outer surface 522 of needle 510 (i.e. ball 922 touches outer wall 522 of needle 510). Shield assembly 900 can slide from this position along needle 510 in a distal direction with very low friction. Ball 922 is radially constrained by the diameter of opening 940, which is sized so that ball 922 cannot escape through opening 940 and out of shield 900. Ball 922 is also radially constrained by needle 510 in the other direction. Spring 911 exerts a force 5 on ball 922 axially, in the distal direction.

Tether or strap 800 is attached to proximal end 909 of first housing 905. It is preferably made in the same molding as first housing 905 but need not be. Tether 800 has distal end 802 (attached to proximal end 909 of first housing 905) and proximal end 804 which extends back and outwards from shield 900. At proximal end 804 is handle 806, which can be grasped by a user. This is molded with strap 800 but can be a separate piece attached to strap 800. Tether or strap 800 is made of a flexible, semi-rigid material such as nylon. Any material that bends but provides some longitudinal compressive strength will be suitable as long as it allows force to be imparted to shield 900 via tether 800.

Needle hub 512 is provided with integrally molded with restraint 514. Restraint 514 has a track 516 along which tether 800 can slide in a distal direction as needle shield 900 slides distally along needle 510. Restraint 514 has stop 518 which prevents further travel of tether 800 when handle 806 reaches stop 518. Restraint 514 has an open channel 520 which allows tether 800 to be placed in track 516 during manufacture but which prevents tether 800 from being easily removed.

Once needle 510 has been used and is to be shielded, the user simply grasps handle 806 and pushes it so that needle shield 900 slides distally along needle 510. When needle shield 900 reaches a point where needle tip 525 passes ball 922, ball 922 is less radially constrained by needle 510 and, urged by spring 911, it begins to move in opening 920, distally and radially. Ball 922 thus moves out of opening 940 and radially inwards further into lumen 913 of shield assembly 900, pivoting about edge 955, which is a wall of opening 940 in second housing 910. When needle tip 525 passes ball 922, needle 510 no longer constrains ball 922. Spring 911 urges ball 922 along opening 920 so that ball 922 pivots about edge 955. Ball 922 is constrained from entering lumen 913 of first housing 905 by the dimensions and geometry of opening 920. Ball 922 thus partially occludes lumen 913.

When ball 922 has moved to a point where it partially occludes lumen 913, handle 806 has reached stop 518, preventing further pushing of handle 806 and hence tether 800. Movement of shield assembly 900 in the distal direction (such that shield assembly 900 slides off distal end 525 of the needle) is prevented by the abutment of stop 518 and handle 806. Movement of the shield assembly in the proximal direction (to expose needle tip 525) is prevented by distal end 525 of needle 510 abutting ball 922.

The length of tether 800 (to tip 525) relative to the length of first housing 905 is set so that when tip 525 is aligned with ball 922, there is sufficient space for the ball to move at least partially into lumen 913. Similar considerations described above in the context of a catheter inserter apply when selecting the angle formed between ball 922 and the part of needle shield 900 that is immediately radially outward of ball 922 and which ball 922 abuts when the shield is deployed. Proximal end 909 of first housing 905 is dimensioned to overhang so that tip 525 can never emerge from distal end 907.

When shield 900 is deployed, part of ball 922 lies in lumen 913 and part of it lies beneath distal end 935 of second housing 910, which radially constrains it. If shield assembly 900 is moved proximally, ball 922 will abut needle tip 525 and be forced against the distal and upper inside walls of second housing 910. Further proximal movement of the shield assembly and hence emergence of needle tip 25 will be prevented.

Lumen 913 is sized such that needle 510 fits relatively snugly in lumen 913. Thus, when needle shield 900 is moved proximally into deployment and ball 922 abuts needle tip 525, needle 510 will not move away from ball 922. Lumen 913 thus provides support opposite ball 922 to prevent needle 510 from wiggling, and to prevent tip 525 from moving such that it pierces first housing 905.

In an alternative embodiment, ball 922 fully enters lumen 913. Ball 922 has a diameter slightly larger than that of lumen 913. In this case, lumen 913 is also dimensioned to provide support for needle 910 opposite ball 922, thus preventing wiggle of the needle and preventing tip 525 from piercing first housing 905.

Figure 28:
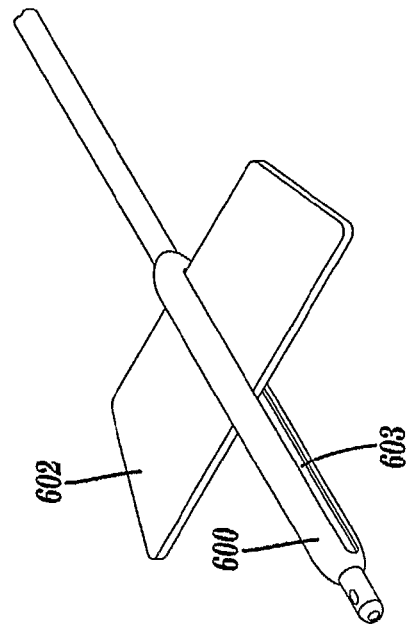
FIGS. 27-30 are isometric views of winged catheter introducers equipped with the needle shield.
Figure 27:
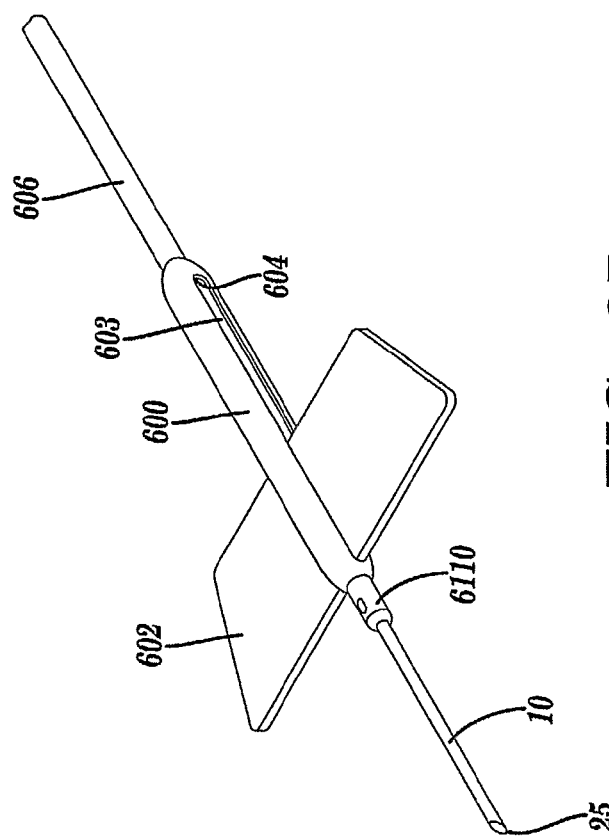

Application of the invention to a winged needle is shown in FIGS. 27 and 28. In that embodiment, shield assembly 6110 (of the type described with reference to FIGS. 9-13) is attached to sheath 600. Sheath 600 has slits 603, which make it slidable over wings 602 and tube 606. Distal movement of shield assembly 6110 is prevented by back 604 of slit 603 abutting wings 602.

Figure 30:
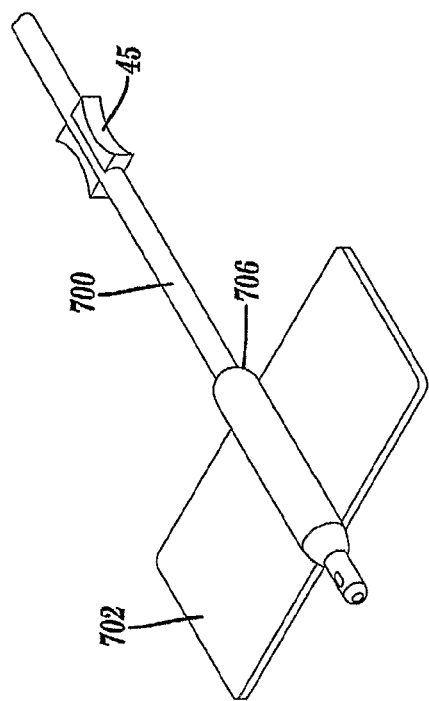
Figure 29:
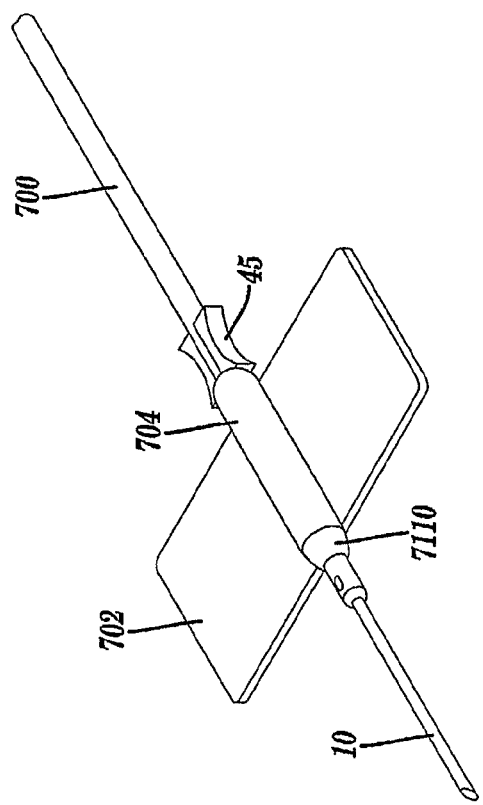

Another winged needle application is shown in FIGS. 29 and 30. In that application, needle assembly 7110 (also of the type described with reference to FIGS. 9-13) is provided with wings 702. Needle hub 45 is squeezed between the finger tips to release it from body tube 704. A flange on tube 700 abuts a collar at 706 to prevent further proximal movement of needle hub 45, at which point needle shield assembly is deployed, preventing distal movement of tip 25.

The invention is shown in the context of a another winged needle (with or without catheter) in FIGS. 31 and 32. In that embodiment, needle hub 845 is attached to first and second wings 802 and 804. Wings 802 and 804 are arranged about tube 806. Wings 802 and 804 respectively have protrusions 812, 814 and 808, 810 which act as hinges allowing some rotation of wings 802 and 804 about tube 806. Protrusion 808 is attached to or abuts needle assembly 8110 at proximal end 8120 and is provided with a short lumen so that protrusion 808 and hence wing 804 can slide axially along needle 10. Protrusion 810 also has a lumen that allows it to slide axially along tube 806. Movement of wing 804 is constrained between protrusions 812 and 814 of wing 802.

When the ball has moved into its shielding position as described above, preventing proximal movement of shield assembly 8110, protrusion 810 of wing 804 abuts protrusion 812 of wing 802, preventing distal movement of wing 804 and hence of shield assembly 8110.

Figure 34:
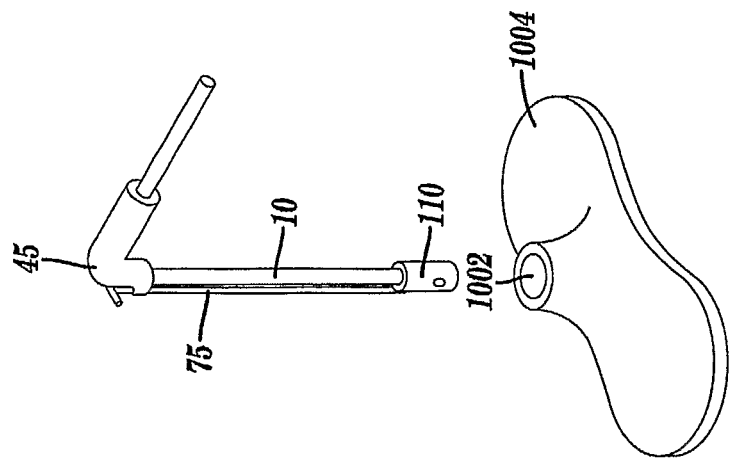
FIGS. 33-34 are isometric views of the needle shield applied to a Huber needle used with an implantable access port.
Figure 33:
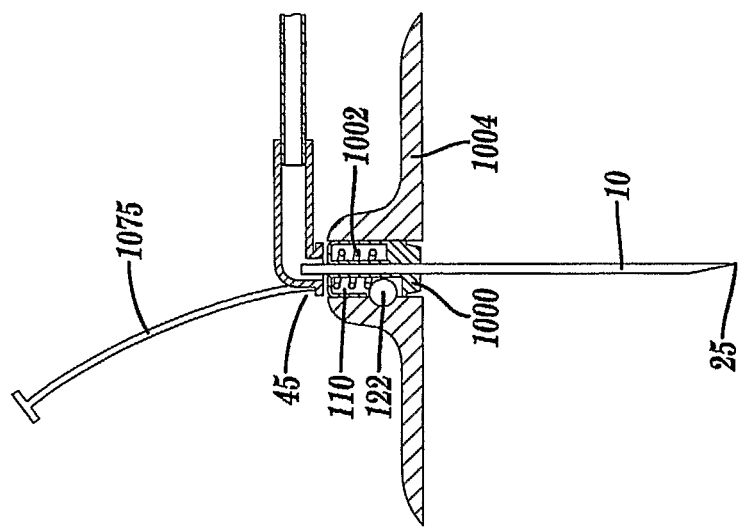

The invention in the context of a Huber needle is shown in FIGS. 33 and 34. In that embodiment, needle hub 1045 is generally L-shaped and tether 1075 is generally parallel to needle 1010, except that it arcs slightly due to gravity. Wing 1004 has an opening 1002, in which needle shield assembly 10110 (of the type described with reference to FIGS. 16-19) resides prior to deployment, locked in place by ball 10122. When needle tip 1025 is shielded, ball 10122 allows shield assembly to be removed from opening 1002. At this point, tether 1075 is fully played out and distal movement of shield assembly 10110 is prevented.

Figure 36:
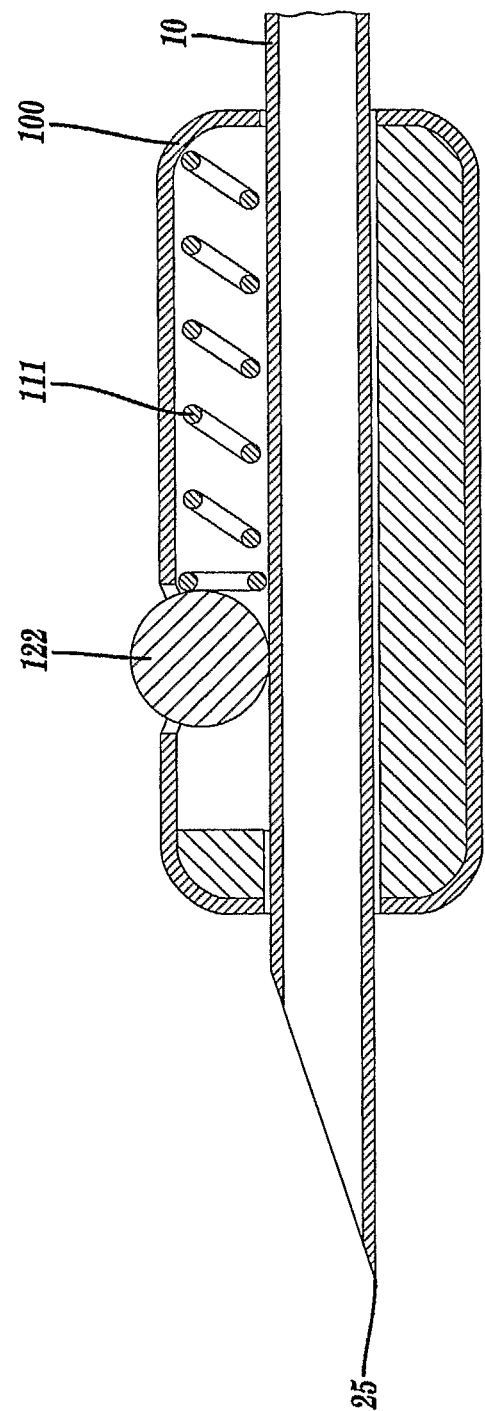
FIGS. 36-51 are orthogonal views of alternative embodiments of the invention.
Figure 37:
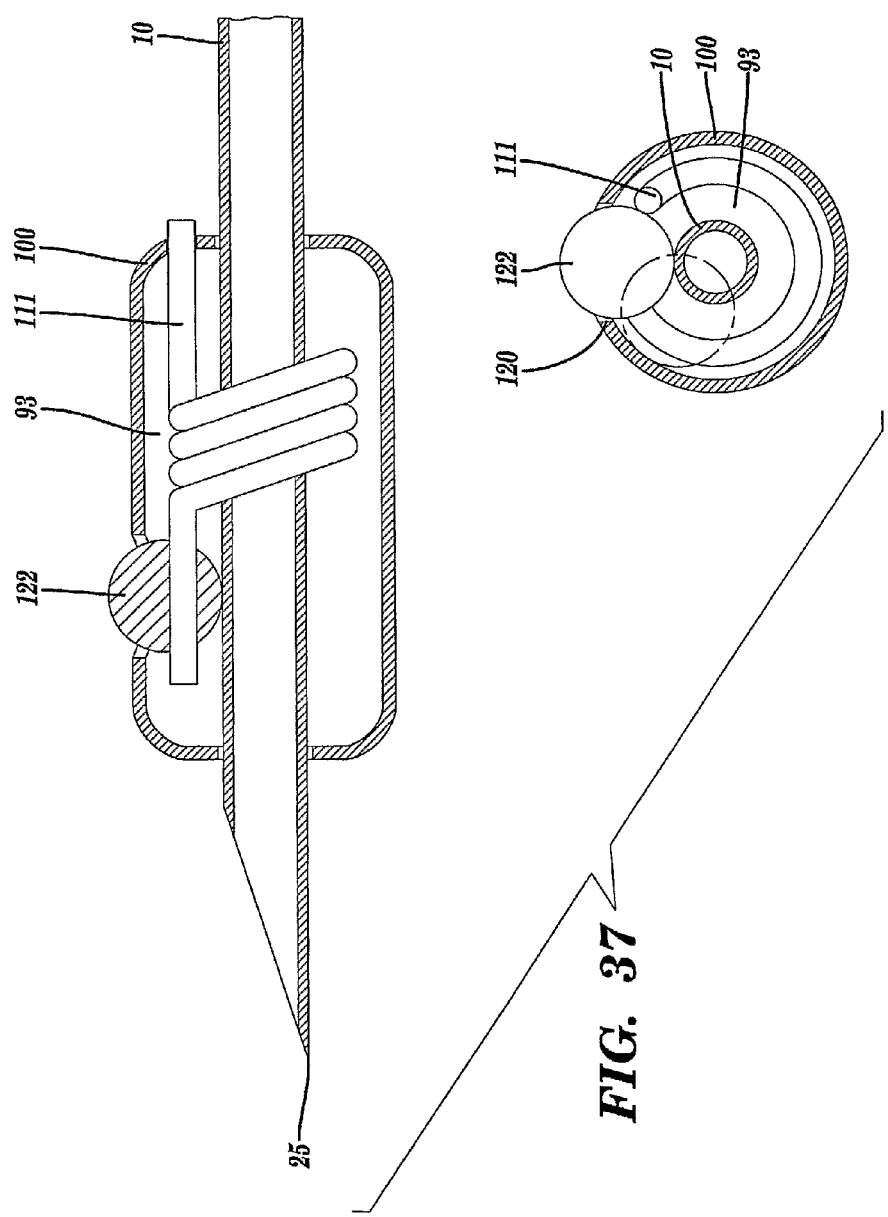
Figure 38:
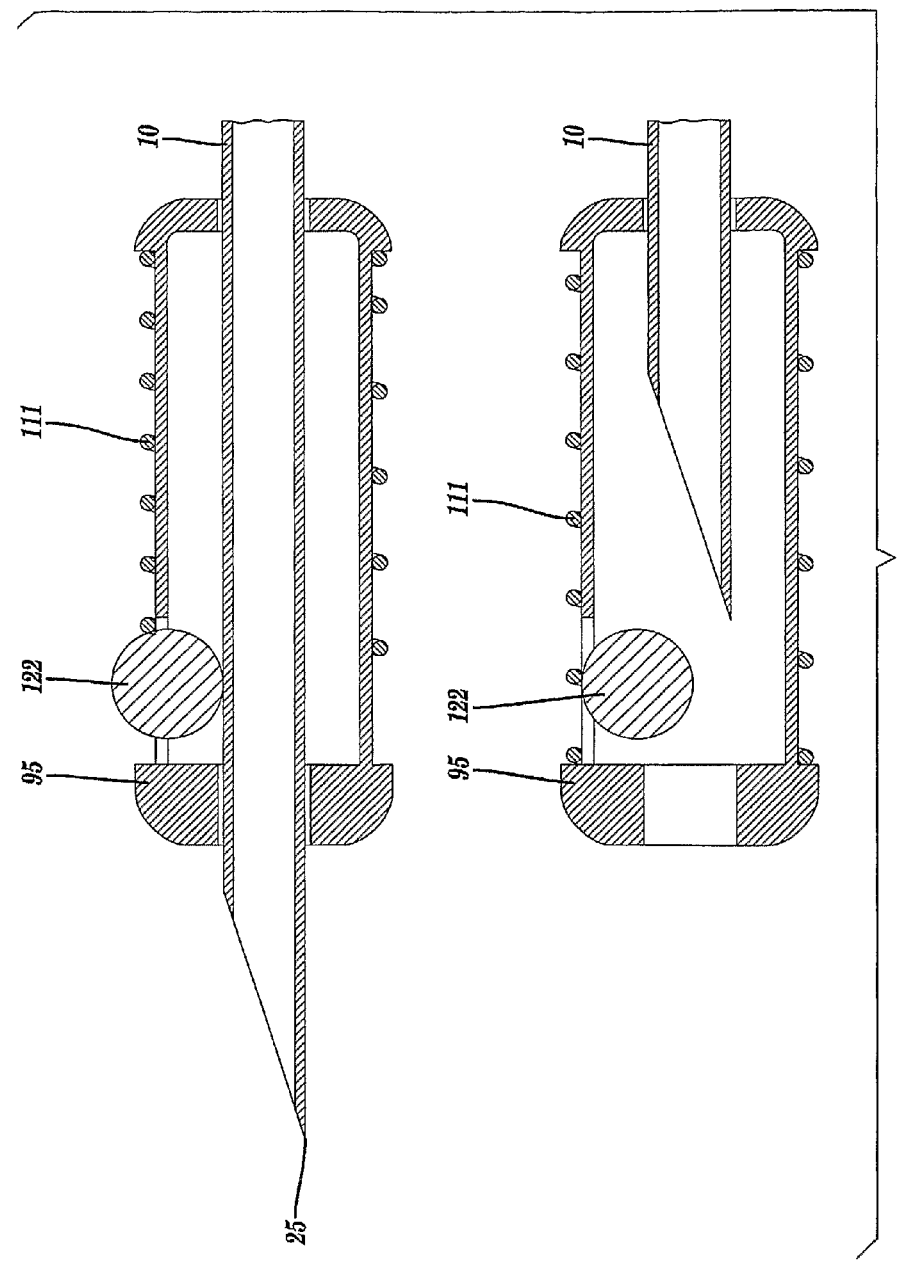
Figure 39:
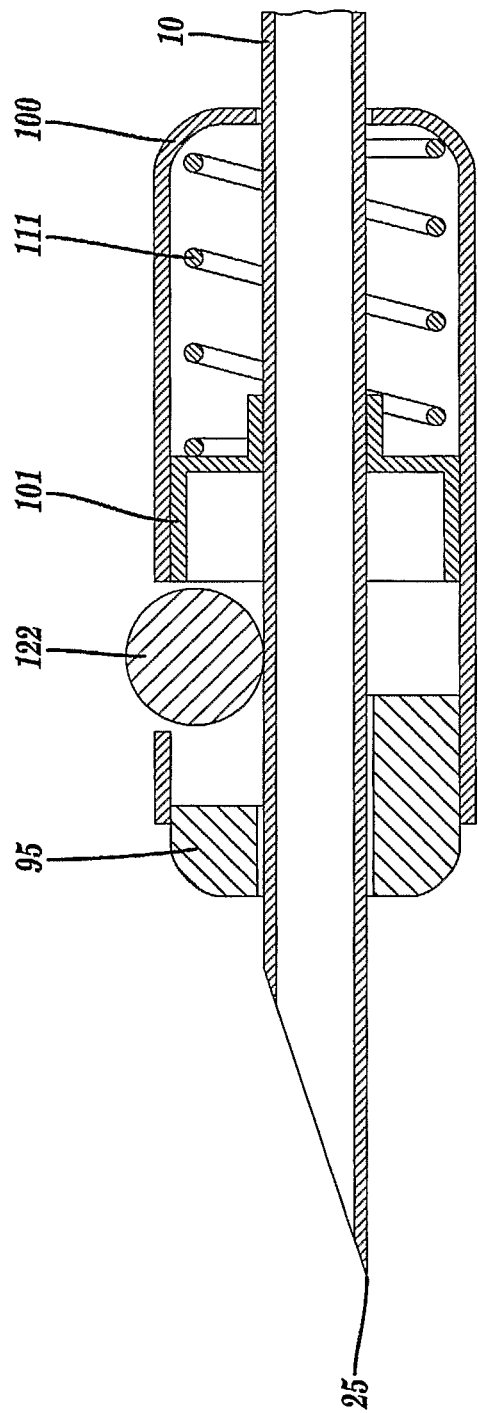
Figure 40:
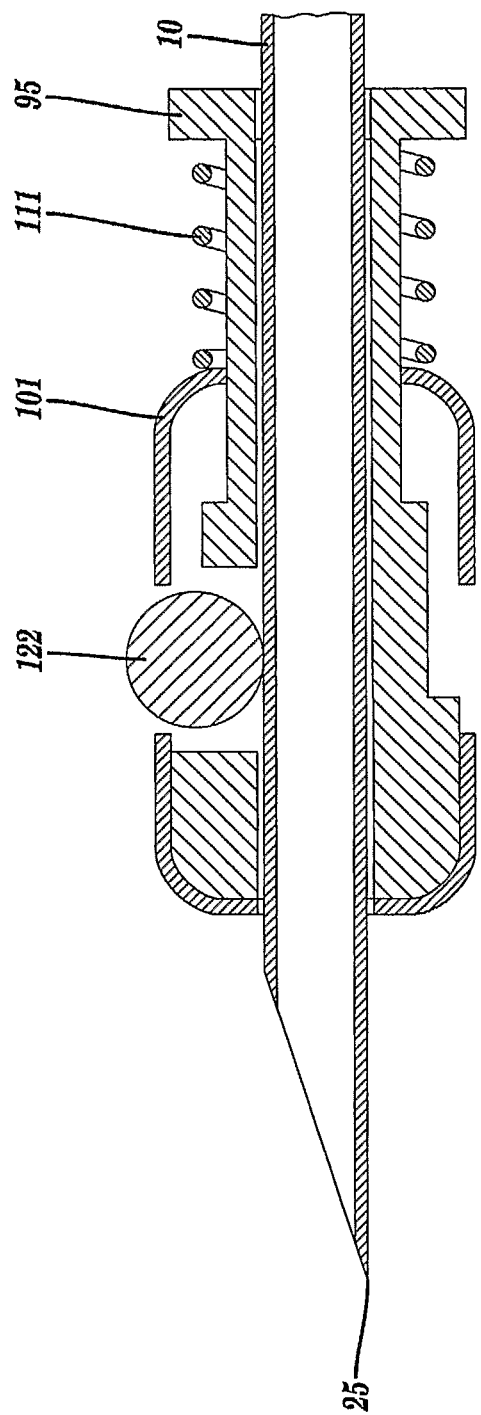

A blood collection device incorporating the shield shown in FIGS. 23-26 is shown in FIG. 35. Some alternative embodiments are shown in FIGS. 36-48. FIG. 36 shows spring 111 lying on one side of needle 10, parallel to the needle axis rather than around needle 10. In FIG. 37 spring 111 is a torsion spring which provides a twisting force around the axis of needle 10. This exerts a circumferential force on ball 122. Opening 120 is configured to allow ball 122 to move circumferentially and towards lumen 93. FIG. 38 shows spring 111 placed outside first housing 95. FIG. 39 shows a piston 101 interposed between spring 111 and ball 122. In FIG. 40 piston 101 is in the form of a cap interposed between spring 111 and ball 122. In this embodiment spring 111 is not enclosed by cap 100.

Figure 41:
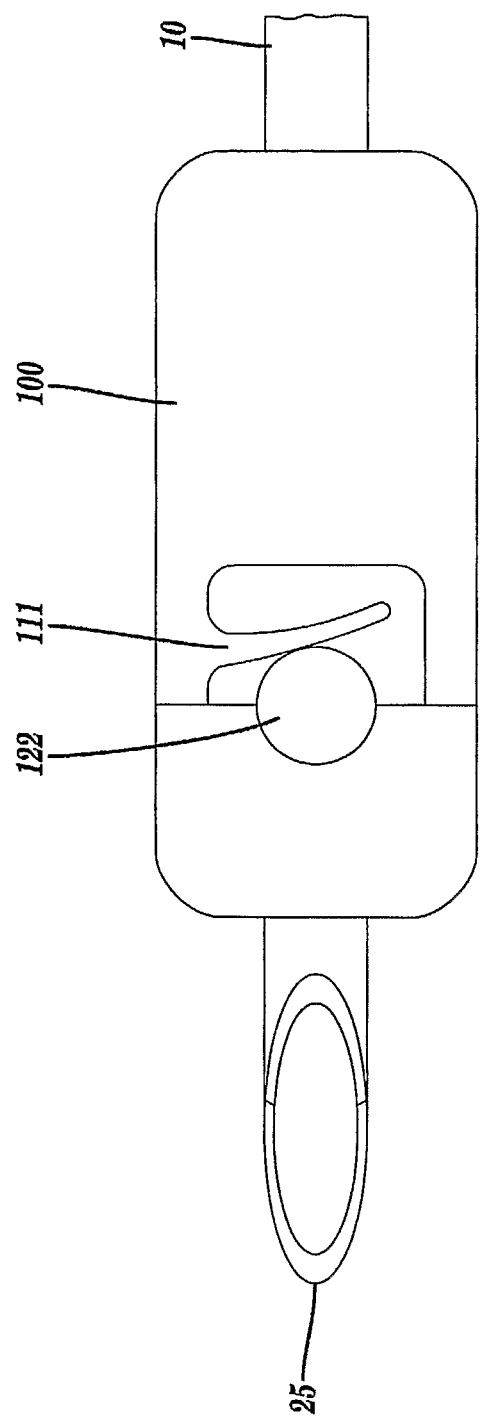
Figure 42:
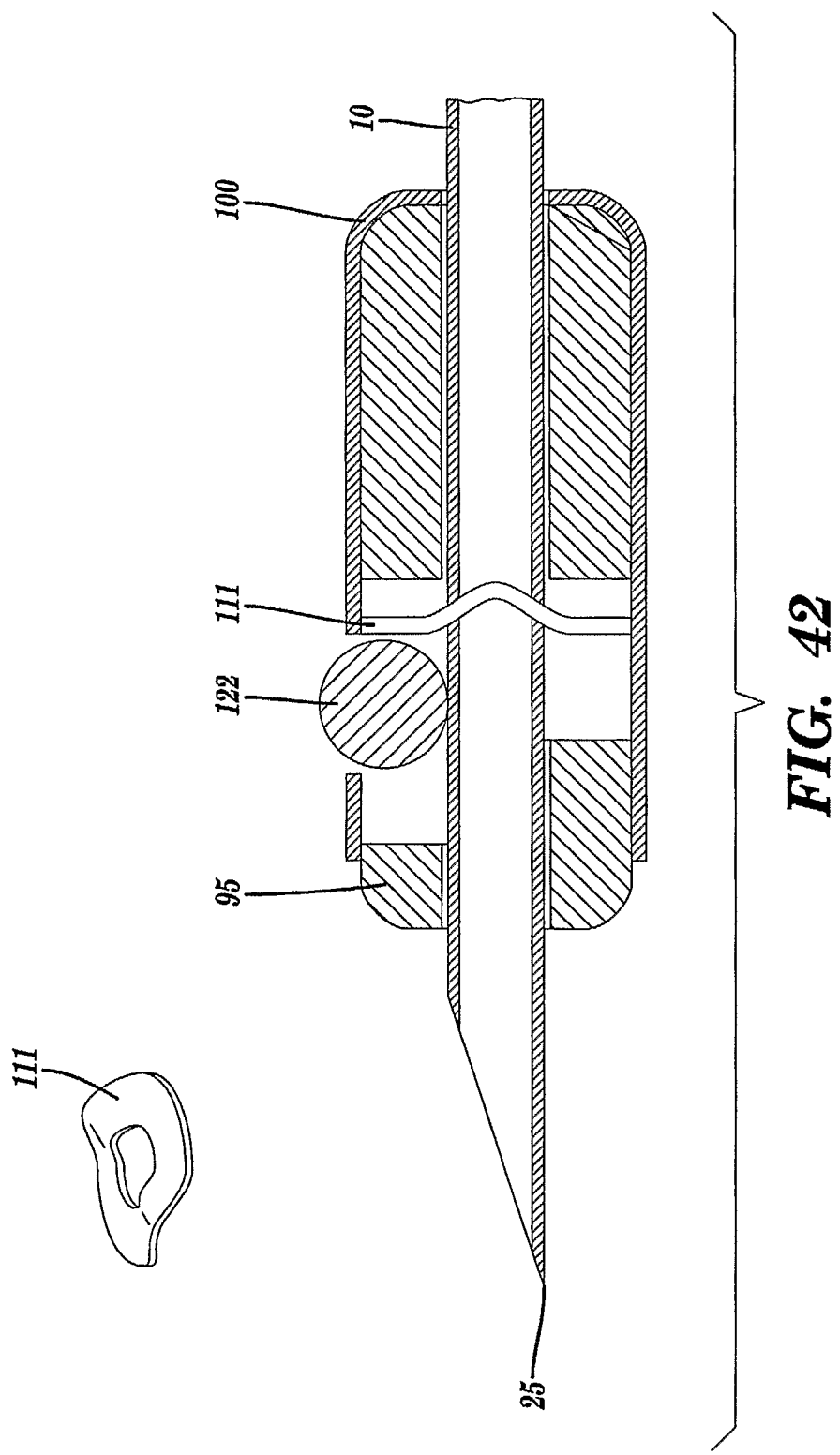

FIG. 41 shows spring 111 in the form of a leaf spring, integral with cap 100. Spring 111 may be a separate member from cap 100 or may be formed with cap 100. FIG. 42 shows a spring 111 in the form of a thin wave washer threaded over needle 10.

Figure 43:
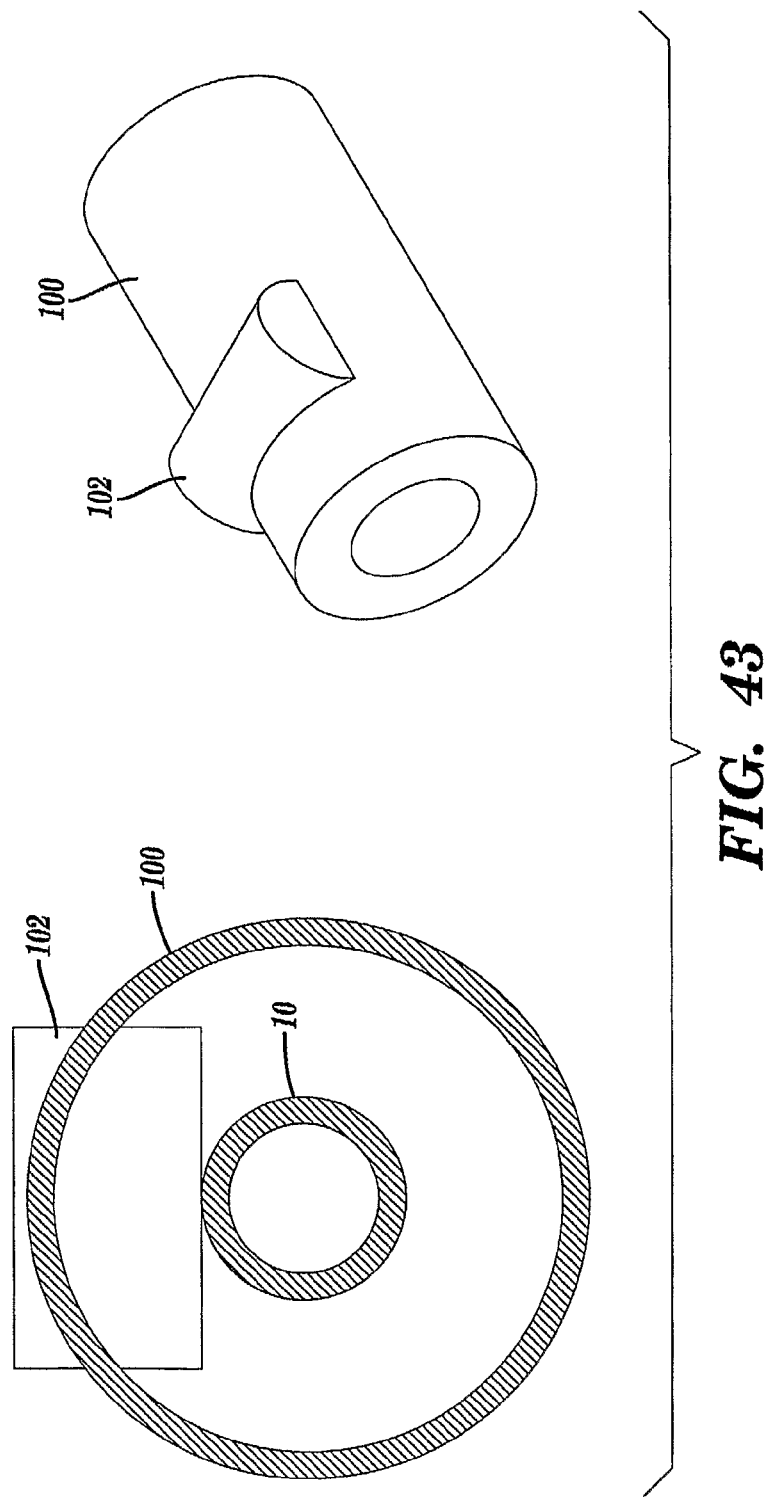

While a sphere is the preferred choice for ball 122, a perfectly spherical object is not essential. In the embodiment of FIG. 43, roller 102 is substituted for ball 122.

Figure 44:
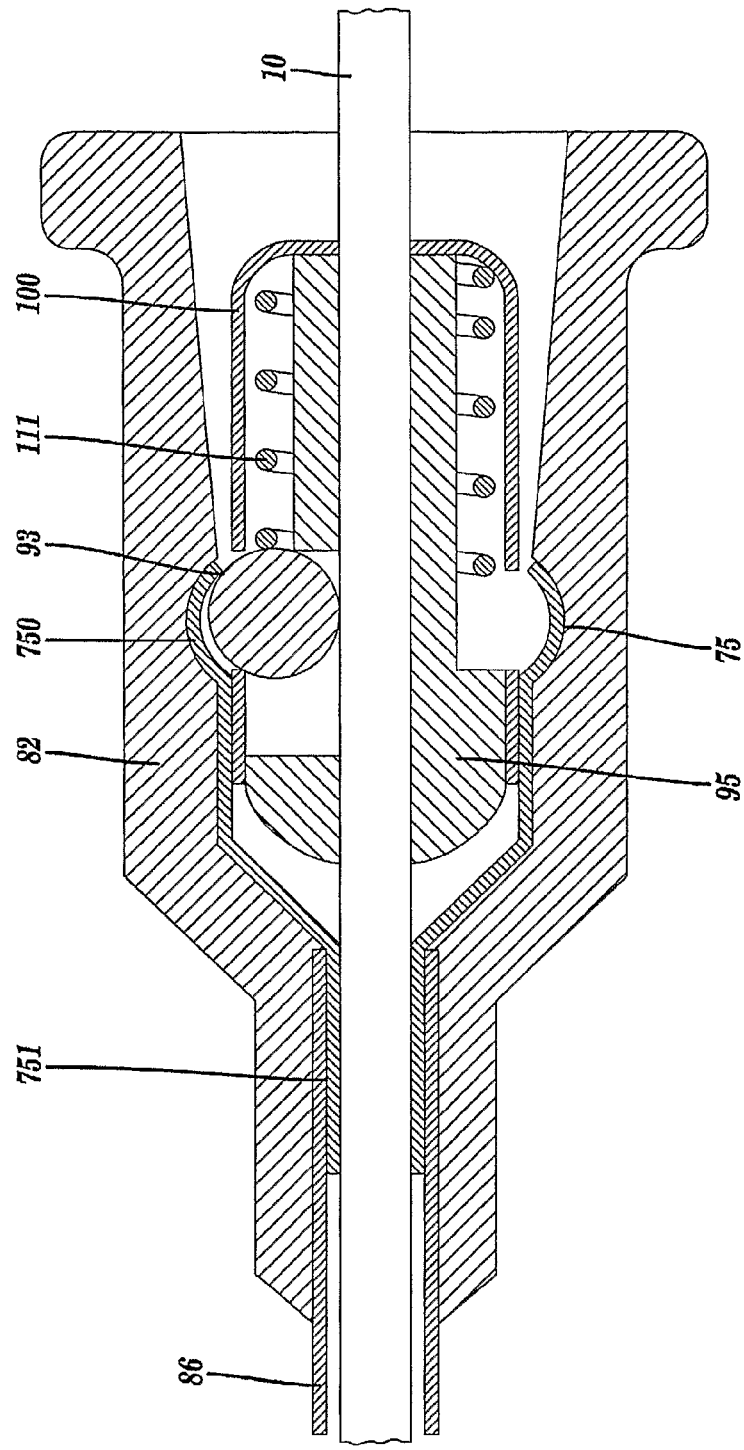

In FIG. 44, groove 75 is lined with metal to provide a high pull out force and to minimize the undercut in catheter 52, thus making it easier to mold catheter hub 52. In this embodiment, metal liner 750 is an extension of metal wedge 751 which secures catheter tube 86 the catheter hub. Metal liner 750 may of course be a separate ring or partial ring.

Figure 45:
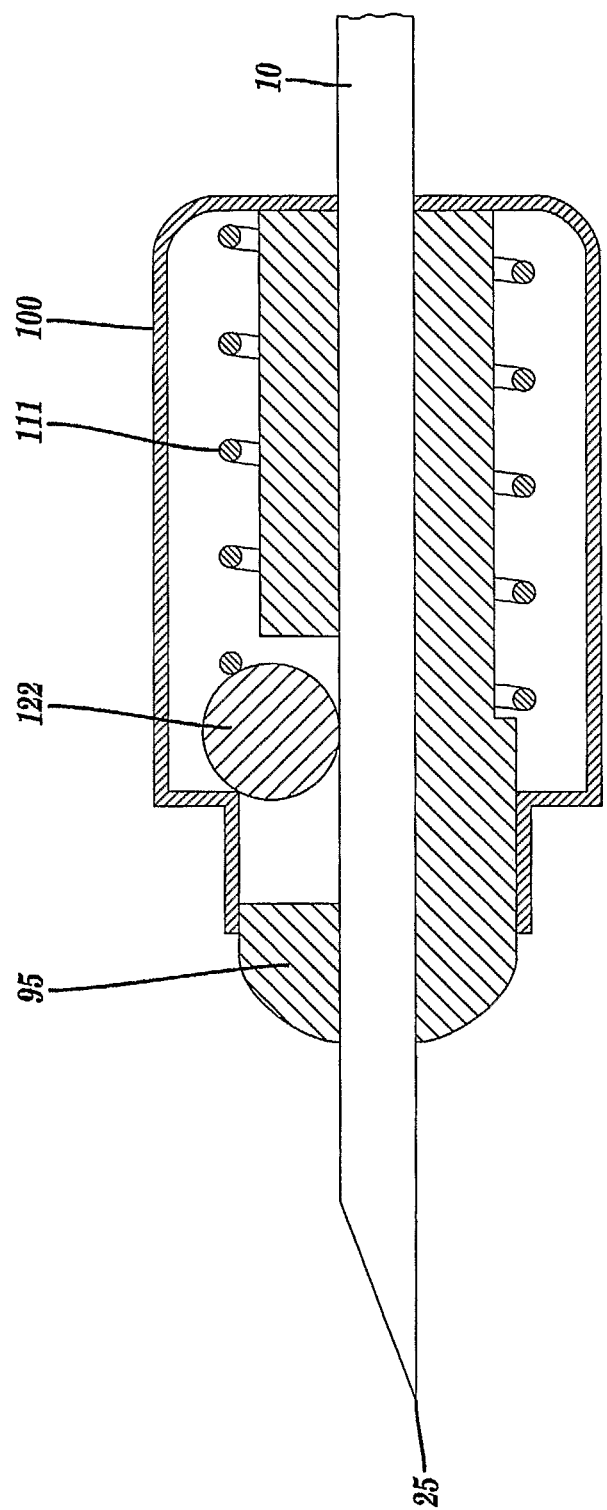
Figure 47:
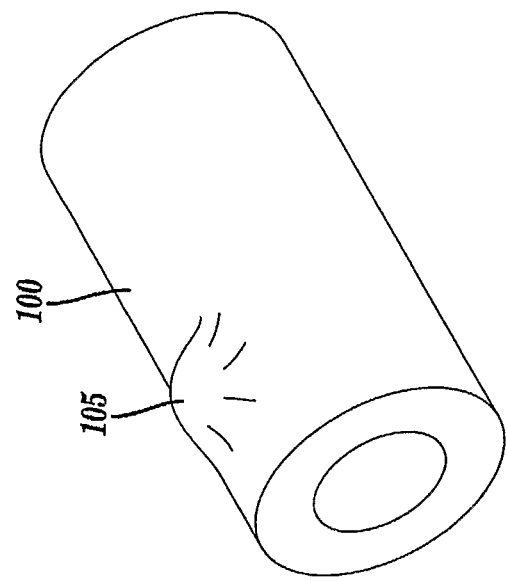
Figure 46:
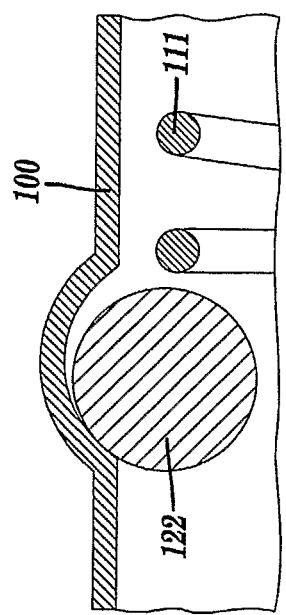

Ball 122 can be enclosed within cap 100 as shown in FIGS. 45-47. In that case, ball 122 does not provide a lock with the catheter hub. In the embodiment shown in FIG. 47, cap 100 is enclosed by flexible metal or plastic skin 105 that covers opening 150 and allows movement of ball 122 so that it can unlock from catheter hub 52. This structure can be replaced by a protrusion formed of rigid metal or circumferential bulge, neck down or channel.

Figure 48:
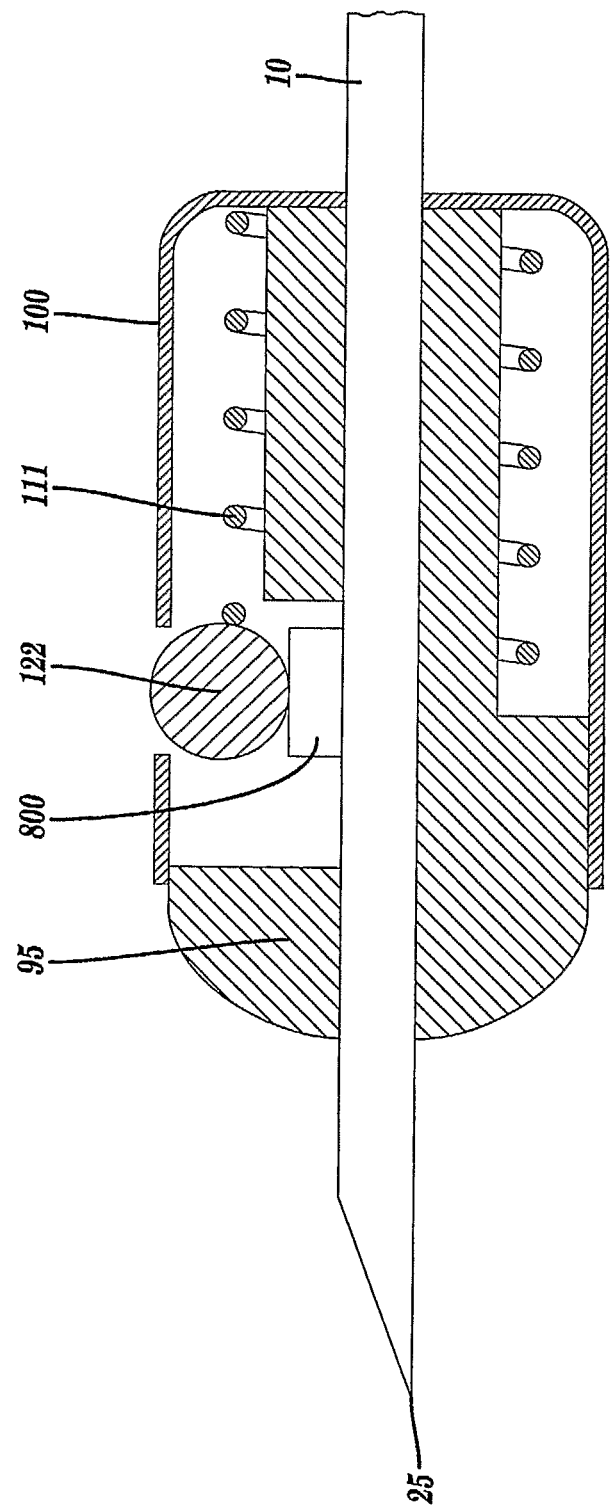

In the embodiment in FIG. 48, ball 122 is seated on piston 800 which abuts needle 10 in the non-deployed position. Piston 800 moves with ball 122 as the shield is deployed. The size of piston 800 changes depending on the gauge of the needle. This embodiment thus allows one size of ball to be used with a variety of needle sizes.

Figure 50:
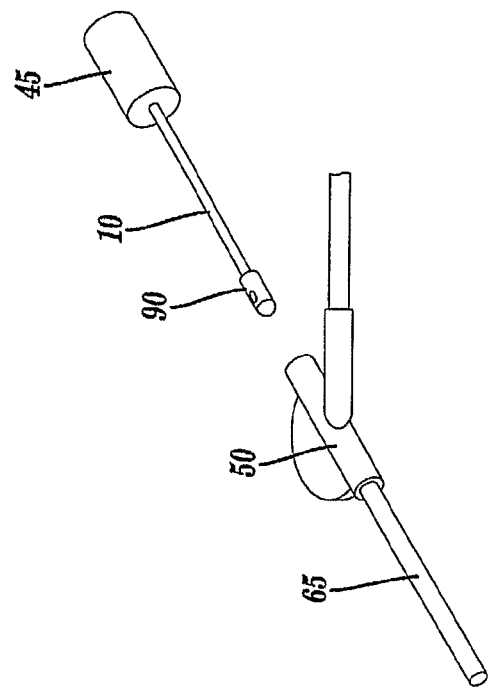
Figure 49:
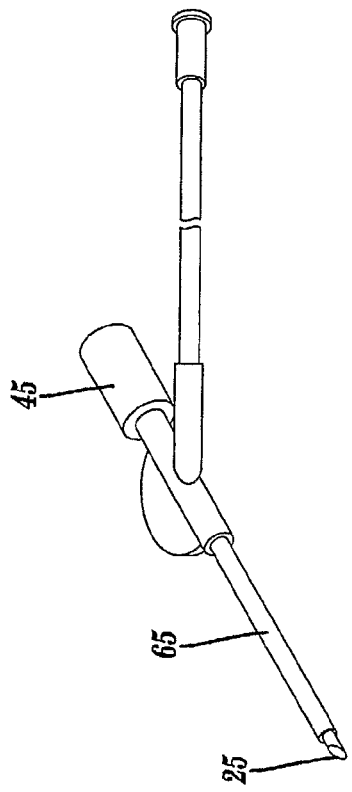
Figure 51:
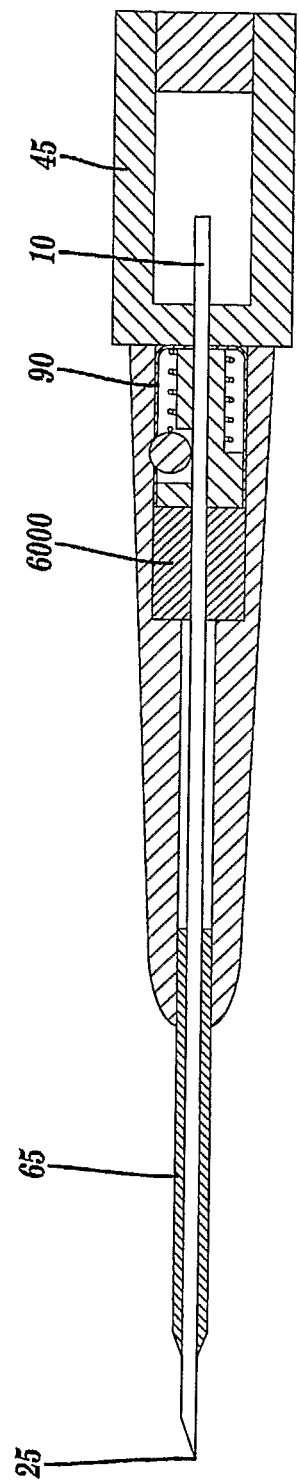

In the embodiment of FIGS. 49-51, the shield assembly described above is applied to a Y shaped catheter introducer assembly in which needle 10 is drawn through a septum 6000.

Although limited embodiments of the needle shield assemblies, their components, and their applications on different needle devices have been specifically described and illustrated, the descriptions are not intended to limit the scope of the basic invention. Many modifications and variations will be apparent to those skilled in the art. Accordingly, it is to be understood that the needle shield assemblies and their components constructed according to principles of this invention may be embodied other than as specifically described herein. The invention is also defined in the following claims.

I claim:

1. A method of making a needle assembly comprising:
providing a needle having a proximal end, a sharp distal end and a longitudinal axis;
providing a needle shield assembly comprising:
a blocking object carrier,
a blocking object having a blocking object axis, and
a lumen coaxial with the longitudinal axis of the needle, the lumen having a proximal end and a distal end,
wherein the blocking object is moveable from a shielding position in which the blocking object at least partially occludes the lumen and a non-shielding position in which the needle can slide along the lumen;
placing the blocking object in the blocking object carrier in the shielding position, wherein in the shielding position, the blocking object carrier holds the blocking object in a position in which the blocking object axis is offset from the longitudinal axis of the needle;
inserting the proximal end of the needle into the distal end of the lumen; and
moving the needle shield assembly such that the needle moves the blocking object from the shielding position to a non-shielding position.

2. The method of claim 1, further comprising the step of attaching a spring to the blocking object carrier such that the spring biases the blocking object towards the longitudinal axis of the needle.

3. The method of claim 1, further comprising the step of threading a catheter tube over the needle.

4. The method of claim 1, further comprising the step of snapping a catheter adapter onto the needle shield assembly.

5. The method of claim 1, wherein the blocking object is a ball.

6. The method of claim 2, wherein the step of attaching a spring to the blocking object carrier comprises the step of threading the spring over the blocking object carrier.

7. The method of claim 3, further comprising the step of placing at least part of the needle shield assembly inside a catheter adapter.

8. The method of claim 3, further comprising the steps of placing a catheter adapter on the needle shield assembly and locking the needle shield assembly to the catheter adapter such that in the shielding position, the blocking object unlocks the needle shield assembly from the catheter adapter and in the non-shielding position, the blocking object locks the catheter adapter to the needle shield assembly.

9. The method of claim 3, further comprising the steps of placing a catheter adapter on the needle shield assembly in the shielding position and moving the needle shield assembly into the non-shielding position, thereby locking the catheter adapter to the needle shield assembly.

* * * * *